US006475718B2

(12) United States Patent
Doms et al.

(10) Patent No.: US 6,475,718 B2
(45) Date of Patent: *Nov. 5, 2002

(54) METHODS AND COMPOSITIONS FOR MODULATING THE INTERACTION BETWEEN THE APJ RECEPTOR AND THE HIV VIRUS

(75) Inventors: Robert W. Doms, Berwyn, PA (US); Daryl Faulds, Mill Valley, CA (US); Joseph E. Hesselgesser, San Francisco, CA (US); Richard Horuk, Belmont, CA (US); Branislava Mitrovic, Walnut Creek, CA (US); Yiqing Zhou, El Sobrante, CA (US)

(73) Assignees: Schering Aktiengesellschaft, Berlin (DE); The Trustees of the University of Pennsylvania, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 43 days.

(21) Appl. No.: 09/149,045

(22) Filed: Sep. 8, 1998

(65) Prior Publication Data

US 2002/0062488 A1 May 23, 2002

(51) Int. Cl.$^7$ .............................. C12Q 1/70; C12N 5/06; C12N 5/08
(52) U.S. Cl. ...................... 435/5; 435/325; 435/352; 435/353; 435/354; 435/358; 435/361; 435/4; 435/366; 435/372; 435/372.3
(58) Field of Search ................................. 435/325, 352, 435/353, 354, 358, 361, 366, 372, 372.3, 4, 5

(56) References Cited

FOREIGN PATENT DOCUMENTS

WO 97/45543 12/1997

OTHER PUBLICATIONS

Linqi Zhang et al., Chemokine Coreceptor Usage by Diverse Primary Isolates of Human Immunodeficiency Virus Type 1, Journal of Virology, vol. 72, No. 11, Nov. 1998, pp. 9307–9312.

Yi–Jun Zhang et al., Use of Coreceptors Other Than CCR5 by Non–Syncytium–Inducing Adult and Pediatric Isolates of Human Immunodeficiency Virus Type 1 Is Rare In Vitro, Journal of Virology, vol. 72, No. 11, Nov. 1998, pp. 9337–9344.

Kazuhiko Tatemoto et al., "Isolation and Characterization of a Novel Endogenous Peptide Ligand for the Human APJ Receptor," Biochemical and Biophysical Research Communications 251, pp. 471–476 (1998).

Trevor L. Hoffman et al.,"HIV Type I Envelope Determinants for Use of the CCR2b, CCR3, STRL33, and APJ Coreceptors," Proc. Natl. Acad. Sci. USA, vol. 95, pp. 11360–11365, Sep. 1998.

Michael Farzan et al., "A Tyrosine–Rich Region in the N Terminus of CCR5 Is Important for Human Immunodeficiency Virus Type 1 Entry and Mediates an Association Between gp120 and CCR5," Journal of Virology, vol. 72, No. 2, Feb. 1998, p. 1160–1164.

Aimee L. Edinger et al., "An Orphan Seven–Transmembrane Domain Receptor Expressed Widley in the Brain Functions as a Coreceptor for Human Immunodeficiency Virus Type 1 and Simian Immunodeficiency Virus," Journal of Virology, vol. 72, No. 10, Oct. 1998, pp. 7934–7940.

Choe et al., "The Orphan Seven–Transmembrane Receptor Apj Supports the Entry of Primary T–Cell–Line–Tropic and Dualtropic Human Immunodeficiency Virus Type 1", J. of Virology, vol. 72, No. 7, Jul. 1998, pp. 6113–6118.

Brian F. O'Dowd et al., "A human gene that shows identity with the gene encoding the angiotensin . . . " Gene, vol. 136, 1993, pp. 355–360.

Choe et al., "The β–Chemokine Receptors CCR3 and CCR5 . . . " Cell, vol. 85, Jun. 28, 1996, pp. 1135–1148.

Feng et al., "HIV–2 Entry cofactor: Functional cDNA cloning of a Seven–Transmembrane . . . ", Science, vol. 272, May 10, 1996, pp. 872–877.

Dragic et al., "HIV–1 entry into CD4+ cells is mediated . . . ", Nature vol. 381, June 20, 1996, pp. 667–673.

Deng et al., "Identification of a major co–receptor . . . ", Nature, vol. 381, Jun. 20, 1996, pp 661–666.

Doranz et al., "A Dual–Tropic Primary HIV–1 Isolate . . . ", Cell, vo. 85, Jun. 28, 1996, pp. 1149–1158.

Matsumoto et al., "Low stringency hybridization study of the dopamine . . . " Neuoroscience Letters, vol. 219, (1996), pp. 119–122.

Dohlman et al., "Model systems for the study of seven–transmembrane–segment receptors", Annu. Rev. Biochem, 1991, vol. 60, pp. 653–688.

Kolson et al., "The Effects of human immunodeficiency virus in the central nervous system", in Ad. in Virus Res., vol. 50, pp. 1–47, Academic Press, 1998.

Rucker et al., "Utilization of Chemokine receptors, Orphan Receptors, . . . ", J. of Virology, vol. 71, pp. 8999–9007, Dec. 1997.

(List continued on next page.)

*Primary Examiner*—Robert D. Budens
(74) *Attorney, Agent, or Firm*—Millen, White, Zelano & Branigan, P.C.

(57) ABSTRACT

The orphan seven transmembrane domain receptor, APJ, can function as a coreceptor for cellular infection by the HIV virus. The establishment of cell lines that coexpress CD4 and APJ provide valuable tools for continuing research on HIV infection and the development of anti-HIV therapeutics.

30 Claims, 11 Drawing Sheets

OTHER PUBLICATIONS

Frazan et al., "Two Orphan Seven–Transmembrane Segment receptors . . . ", J. Exp. Med., vol. 186, No. 3, pp. 405–411, Aug. 4, 1997.

Liao et al., "STRL33, A Novel Chemokine Receptor–like Protein . . . " J. of Exp. med., vol. 185, No. 11, pp 2015–2023, Jun. 2, 1997.

Reeves et al., "CD4–Independent Infection by HIV–2 (ROD/B): Use of the 7–Transmembrane . . . ", Virology, vol. 231, pp. 130–134 (1997).

He et al., "CCR3 and CCR5 are co–receptors for HIV–1 infection of microglia", Nature, vol. 385, pp. 645–649, Feb. 1997.

Wiley et al., "Cellular localization of human immunodeficiency virus infection . . . ", Proc. Natl. Acad. Sci. USA, vol. 83, pp. 7089–7093, Sep. 1986.

Pleskoff et al., "Identification of a Chemokine receptor Encoded by . . . ", Science, vol. 276, pp. 1874–1878, Jun. 20, 1997.

Deng et al., "Expression cloning of new receptors used by simian and human immunodeficiency viruses", Nature, vol. 388, pp. 296–300, Jul. 17, 1997.

Bagasra et al., "Cellular reservoirs of HIV–1 in the central nervous system of infected individuals: identification by the combination . . . ", AIDS, vol. 10, pp. 573–585, 1996.

```
caggagacag gcttcctcca gggtctggag aacccagagg cagctcctcc tgagtgctgg   60
gaaggactct gggcatcttc agcccttctt actctctgag gctcaagcca gaaattcagg  120
ctgcttgcag agtgggtgac agagccacgg agctggtgtc cctgggaccc tctgcccgtc  180
ttctctccac tccccagc atg gag gaa ggt ggt gat ttt gac aac tac tat   231
                    Met Glu Glu Gly Gly Asp Phe Asp Asn Tyr Tyr
                     1               5                        10 ggg gca gac aac cag tct gag tgt gag tac aca gac tgg aaa tcc tcg   279
Gly Ala Asp Asn Gln Ser Glu Cys Glu Tyr Thr Asp Trp Lys Ser Ser
            15                  20                  25 ggg gcc ctc atc cct gcc atc tac atg ttg gtc ttc ctc ctg ggc acc   327
Gly Ala Leu Ile Pro Ala Ile Tyr Met Leu Val Phe Leu Leu Gly Thr
            30                  35                  40 acg gga aac ggt ctg gtg ctc tgg acc gtg ttt cgg agc agc cgg gag   375
Thr Gly Asn Gly Leu Val Leu Trp Thr Val Phe Arg Ser Ser Arg Glu
            45                  50                  55 aag agg cgc tca gct gat atc ttc att gct agc ctg gcg gtg gct gac   423
Lys Arg Arg Ser Ala Asp Ile Phe Ile Ala Ser Leu Ala Val Ala Asp
 60                  65                  70                  75 ctg acc ttc gtg gtg acg ctg ccc ctg tgg gct acc tac acg tac cgg   471
Leu Thr Phe Val Val Thr Leu Pro Leu Trp Ala Thr Tyr Thr Tyr Arg
                    80                  85                  90 gac tat gac tgg ccc ttt ggg acc ttc ttc tgc aag ctc agc agc tac   519
Asp Tyr Asp Trp Pro Phe Gly Thr Phe Phe Cys Lys Leu Ser Ser Tyr
                95                 100                 105
```

FIG. 9

```
ctc atg ctc gtc aac atg tac gcc agc gtc ttc tgc ctc acc ggc ctc    567
Leu Met Leu Val Asn Met Tyr Ala Ser Val Phe Cys Leu Thr Gly Leu
        110                 115                 120 agc ttc gac cgc tac ctg gcc atc gtg agg cca gtg gcc aat gct cgg    615
Ser Phe Asp Arg Tyr Leu Ala Ile Val Arg Pro Val Ala Asn Ala Arg
        125                 130                 135 ctg agg ctg cgg gtc agc ggg gcc gtg gcc acg gca gtt ctt tgg gtg    663
Leu Arg Leu Arg Val Ser Gly Ala Val Ala Thr Ala Val Leu Trp Val
140                 145                 150                 155 ctg gcc gcc ctc ctg gcc atg cct gtc atg gtg tta cgc acc acc ggg    711
Leu Ala Ala Leu Leu Ala Met Pro Val Met Val Leu Arg Thr Thr Gly
                160                 165                 170 gac ttg gag aac acc act aag gtg cag tgc tac atg gac tac tcc atg    759
Asp Leu Glu Asn Thr Thr Lys Val Gln Cys Tyr Met Asp Tyr Ser Met
            175                 180                 185 gtg gcc act gtg agc tca gag tgg gcc tgg gag gtg ggc ctt ggg gtc    807
Val Ala Thr Val Ser Ser Glu Trp Ala Trp Glu Val Gly Leu Gly Val
        190                 195                 200 tcg tcc acc acc gtg ggc ttt gtg gtg ccc ttc acc atc atg ctg acc    855
Ser Ser Thr Thr Val Gly Phe Val Val Pro Phe Thr Ile Met Leu Thr
        205                 210                 215 tgt tac ttc ttc atc gcc caa acc atc gct ggc cac ttc cgc aag gaa    903
Cys Tyr Phe Phe Ile Ala Gln Thr Ile Ala Gly His Phe Arg Lys Glu
220                 225                 230                 235 cgc atc gag ggc ctg cgg aag cgg cgg ctg ctc agc atc atc gtg        951
Arg Ile Glu Gly Leu Arg Lys Arg Arg Leu Leu Ser Ile Ile Val
                240                 245                 250
```

FIG. 9

```
gtg ctg gtg gtg acc ttt gcc ctg tgc tgg atg ccc tac cac ctg gtg   999
Val Leu Val Val Thr Phe Ala Leu Cys Trp Met Pro Tyr His Leu Val
            255                 260                 265 aag acg ctg tac atg ctg ggc agc ctg ctg cac tgg ccc tgt gac ttt  1047
Lys Thr Leu Tyr Met Leu Gly Ser Leu Leu His Trp Pro Cys Asp Phe
            270                 275                 280 gac ctc ttc ctc atg aac atc ttc ccc tac tgc acc tgc atc agc tac  1095
Asp Leu Phe Leu Met Asn Ile Phe Pro Tyr Cys Thr Cys Ile Ser Tyr
            285                 290                 295 gtc aac agc tgc ctc aac ccc ttc ctc tat gcc ttt ttc gac ccc cgc  1143
Val Asn Ser Cys Leu Asn Pro Phe Leu Tyr Ala Phe Phe Asp Pro Arg
300             305                 310                 315 ttc cgc cag gcc tgc acc tcc atg ctc tgc tgt ggc cag agc agg tgc  1191
Phe Arg Gln Ala Cys Thr Ser Met Leu Cys Cys Gly Gln Ser Arg Cys
                320                 325                 330 gca ggc acc tcc cac agc agc agt ggg gag aag tca gcc agc tac tct  1239
Ala Gly Thr Ser His Ser Ser Ser Gly Glu Lys Ser Ala Ser Tyr Ser
                335                 340                 345 tcg ggg cac agc cag ggg ccc ggc ccc aac atg ggc aag ggt gga gaa  1287
Ser Gly His Ser Gln Gly Pro Gly Pro Asn Met Gly Lys Gly Gly Glu
            350                 355                 360 cag atg cac gag aaa tcc atc ccc tac agc cag gag acc ctt gtg gtt  1335
Gln Met His Glu Lys Ser Ile Pro Tyr Ser Gln Glu Thr Leu Val Val
            365                 370                 375 gac tagggctggg agcagagaga agcctggcgc cctcggccct ccccggcctt        1388
Asp
380 tgcccttgct ttctgaaaat caggtagtgt ggctactcct tgtcctatgc acatcctta  1448 actgtcccct gattct                                                 1464
```

FIG. 9

SEQUENCE LISTING

```
<160> NUMBER OF SEQ ID NOS: 8

<210> SEQ ID NO 1
<211> LENGTH: 1464
<212> TYPE: DNA
<213> ORGANISM: Homo sapiens
<220> FEATURE:
<221> NAME/KEY: CDS
<222> LOCATION: (199)..(1338)

<400> SEQUENCE: 1
caggagacag gcttcctcca gggtctggag aacccagagg cagctcctcc tgagtgctgg      60
gaaggactct gggcatcttc agcccttctt actctctgag gctcaagcca gaaattcagg     120
ctgcttgcag agtgggtgac agagccacgg agctggtgtc cctgggaccc tctgcccgtc     180
ttctctccac tccccagc atg gag gaa ggt ggt gat ttt gac aac tac tat     231
                     Met Glu Glu Gly Gly Asp Phe Asp Asn Tyr Tyr
                      1               5                   10
```

-continued

| | |
|---|---|
| ggg gca gac aac cag tct gag tgt gag tac aca gac tgg aaa tcc tcg<br>Gly Ala Asp Asn Gln Ser Glu Cys Glu Tyr Thr Asp Trp Lys Ser Ser<br>             15                  20                 25 | 279 |
| ggg gcc ctc atc cct gcc atc tac atg ttg gtc ttc ctc ctg ggc acc<br>Gly Ala Leu Ile Pro Ala Ile Tyr Met Leu Val Phe Leu Leu Gly Thr<br>             30                  35                  40 | 327 |
| acg gga aac ggt ctg gtg ctc tgg acc gtg ttt cgg agc agc cgg gag<br>Thr Gly Asn Gly Leu Val Leu Trp Thr Val Phe Arg Ser Ser Arg Glu<br>             45                  50                55 | 375 |
| aag agg cgc tca gct gat atc ttc att gct agc ctg gcg gtg gct gac<br>Lys Arg Arg Ser Ala Asp Ile Phe Ile Ala Ser Leu Ala Val Ala Asp<br>60                  65                70                75 | 423 |
| ctg acc ttc gtg gtg acg ctg ccc ctg tgg gct acc tac acg tac cgg<br>Leu Thr Phe Val Val Thr Leu Pro Leu Trp Ala Thr Tyr Thr Tyr Arg<br>                 80                  85                90 | 471 |
| gac tat gac tgg ccc ttt ggg acc ttc ttc tgc aag ctc agc agc tac<br>Asp Tyr Asp Trp Pro Phe Gly Thr Phe Phe Cys Lys Leu Ser Ser Tyr<br>             95                  100              105 | 519 |
| ctc atg ctc gtc aac atg tac gcc agc gtc ttc tgc ctc acc ggc ctc<br>Leu Met Leu Val Asn Met Tyr Ala Ser Val Phe Cys Leu Thr Gly Leu<br>             110                115              120 | 567 |
| agc ttc gac cgc tac ctg gcc atc gtg agg cca gtg gcc aat gct cgg<br>Ser Phe Asp Arg Tyr Leu Ala Ile Val Arg Pro Val Ala Asn Ala Arg<br>             125                130              135 | 615 |
| ctg agg ctg cgg gtc agc ggg gcc gtg gcc acg gca gtt ctt tgg gtg<br>Leu Arg Leu Arg Val Ser Gly Ala Val Ala Thr Ala Val Leu Trp Val<br>140                 145                150              155 | 663 |
| ctg gcc gcc ctc ctg gcc atg cct gtc atg gtg tta cgc acc acc ggg<br>Leu Ala Ala Leu Leu Ala Met Pro Val Met Val Leu Arg Thr Thr Gly<br>             160                165              170 | 711 |
| gac ttg gag aac acc act aag gtg cag tgc tac atg gac tac tcc atg<br>Asp Leu Glu Asn Thr Thr Lys Val Gln Cys Tyr Met Asp Tyr Ser Met<br>             175                180              185 | 759 |
| gtg gcc act gtg agc tca gag tgg gcc tgg gag gtg ggc ctt ggg gtc<br>Val Ala Thr Val Ser Ser Glu Trp Ala Trp Glu Val Gly Leu Gly Val<br>             190                195              200 | 807 |
| tcg tcc acc acc gtg ggc ttt gtg gtg ccc ttc acc atc atg ctg acc<br>Ser Ser Thr Thr Val Gly Phe Val Val Pro Phe Thr Ile Met Leu Thr<br>             205                210              215 | 855 |
| tgt tac ttc ttc atc gcc caa acc atc gct ggc cac ttc cgc aag gaa<br>Cys Tyr Phe Phe Ile Ala Gln Thr Ile Ala Gly His Phe Arg Lys Glu<br>220                 225                230              235 | 903 |
| cgc atc gag ggc ctg cgg aag cgg cgc cgg ctg ctc agc atc atc gtg<br>Arg Ile Glu Gly Leu Arg Lys Arg Arg Arg Leu Leu Ser Ile Ile Val<br>             240                245              250 | 951 |
| gtg ctg gtg gtg acc ttt gcc ctg tgc tgg atg ccc tac cac ctg gtg<br>Val Leu Val Val Thr Phe Ala Leu Cys Trp Met Pro Tyr His Leu Val<br>             255                260              265 | 999 |
| aag acg ctg tac atg ctg ggc agc ctg ctg cac tgg ccc tgt gac ttt<br>Lys Thr Leu Tyr Met Leu Gly Ser Leu Leu His Trp Pro Cys Asp Phe<br>             270                275              280 | 1047 |
| gac ctc ttc ctc atg aac atc ttc ccc tac tgc acc tgc atc agc tac<br>Asp Leu Phe Leu Met Asn Ile Phe Pro Tyr Cys Thr Cys Ile Ser Tyr<br>             285                290              295 | 1095 |
| gtc aac agc tgc ctc aac ccc ttc ctc tat gcc ttt ttc gac ccc cgc<br>Val Asn Ser Cys Leu Asn Pro Phe Leu Tyr Ala Phe Phe Asp Pro Arg<br>300                 305                310              315 | 1143 |
| ttc cgc cag gcc tgc acc tcc atg ctc tgc tgt ggc cag agc agg tgc<br>Phe Arg Gln Ala Cys Thr Ser Met Leu Cys Cys Gly Gln Ser Arg Cys | 1191 |

```
                     320                 325                 330
gca ggc acc tcc cac agc agc agt ggg gag aag tca gcc agc tac tct      1239
Ala Gly Thr Ser His Ser Ser Ser Gly Glu Lys Ser Ala Ser Tyr Ser
                335                 340                 345 tcg ggg cac agc cag ggg ccc ggc ccc aac atg ggc aag ggt gga gaa      1287
Ser Gly His Ser Gln Gly Pro Gly Pro Asn Met Gly Lys Gly Gly Glu
            350                 355                 360 cag atg cac gag aaa tcc atc ccc tac agc cag gag acc ctt gtg gtt      1335
Gln Met His Glu Lys Ser Ile Pro Tyr Ser Gln Glu Thr Leu Val Val
365                 370                 375 gac tagggctggg agcagagaga agcctggcgc cctcggccct ccccggcctt           1388
Asp
380 tgcccttgct ttctgaaaat caggtagtgt ggctactcct tgtcctatgc acatcccttta  1448 actgtcccct gattct                                                    1464

<210> SEQ ID NO 2
<211> LENGTH: 380
<212> TYPE: PRT
<213> ORGANISM: Homo sapiens

<400> SEQUENCE: 2

Met Glu Glu Gly Gly Asp Phe Asp Asn Tyr Tyr Gly Ala Asp Asn Gln
 1               5                   10                  15

Ser Glu Cys Glu Tyr Thr Asp Trp Lys Ser Ser Gly Ala Leu Ile Pro
                20                  25                  30

Ala Ile Tyr Met Leu Val Phe Leu Leu Gly Thr Thr Gly Asn Gly Leu
            35                  40                  45

Val Leu Trp Thr Val Phe Arg Ser Ser Arg Glu Lys Arg Arg Ser Ala
        50                  55                  60

Asp Ile Phe Ile Ala Ser Leu Ala Val Ala Asp Leu Thr Phe Val Val
 65                 70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Met Leu Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
```

```
                260               265              270
Leu Gly Ser Leu Leu His Trp Pro Cys Asp Phe Asp Leu Phe Leu Met
            275             280             285

Asn Ile Phe Pro Tyr Cys Thr Cys Ile Ser Tyr Val Asn Ser Cys Leu
        290             295             300

Asn Pro Phe Leu Tyr Ala Phe Phe Asp Pro Arg Phe Arg Gln Ala Cys
305             310             315             320

Thr Ser Met Leu Cys Cys Gly Gln Ser Arg Cys Ala Gly Thr Ser His
                325             330             335

Ser Ser Ser Gly Glu Lys Ser Ala Ser Tyr Ser Ser Gly His Ser Gln
            340             345             350

Gly Pro Gly Pro Asn Met Gly Lys Gly Gly Glu Gln Met His Glu Lys
            355             360             365

Ser Ile Pro Tyr Ser Gln Glu Thr Leu Val Val Asp
        370             375             380

<210> SEQ ID NO 3
<211> LENGTH: 4
<212> TYPE: PRT
<213> ORGANISM: Homo sapiens

<400> SEQUENCE: 3

Asn Tyr Tyr Gly
  1

<210> SEQ ID NO 4
<211> LENGTH: 23
<212> TYPE: DNA
<213> ORGANISM: Homo sapiens

<400> SEQUENCE: 4
acaagctagt acccagttga gcc                                         23

<210> SEQ ID NO 5
<211> LENGTH: 22
<212> TYPE: DNA
<213> ORGANISM: Homo sapiens

<400> SEQUENCE: 5
cacacactac ttgaagcact ca                                          22

<210> SEQ ID NO 6
<211> LENGTH: 21
<212> TYPE: DNA
<213> ORGANISM: Homo sapiens

<400> SEQUENCE: 6
atctacaagg gactttcccg c                                           21

<210> SEQ ID NO 7
<211> LENGTH: 21
<212> TYPE: DNA
<213> ORGANISM: Homo sapiens

<400> SEQUENCE: 7
tacacagact ggaaatcctc g                                           21

<210> SEQ ID NO 8
<211> LENGTH: 21
<212> TYPE: DNA
<213> ORGANISM: Homo sapiens
```

-continued

<400> SEQUENCE: 8
tgcaccttag tggtgttctc c                21

METHODS AND COMPOSITIONS FOR MODULATING THE INTERACTION BETWEEN THE APJ RECEPTOR AND THE HIV VIRUS

BACKGROUND OF THE INVENTION

The entry of HIV-1 into cells involves binding of the viral envelope (env) protein to CD4 followed by interaction with one of several coreceptors (reviewed in E. A. Berger, 1997, *AIDS*, 11:S3-S16; Broder et al., 1997, *J. Leukocyte Biol.*, 62:20–29; Doms et al., 1997, *Virology*, 235:279–190; and Moore et al., 1997, *Curr. Opinion Immunol.*, 9:551–562). Binding of the env protein to the appropriate coreceptor is thought to trigger conformational changes in env that mediate fusion between the viral membrane and the host cell membrane. The CCR5 and CXCR4 chemokine receptors have been identified as major HIV-1 coreceptors in that all HIV-1 strains examined to date use one or both of these molecules as second receptors. CCR5 supports infection by R5 (M-tropic) virus strains, while CXCR4 supports infection by X4 (T-tropic) virus isolates (Alkhatib et al., 1996, *Science*, 272:1955–1958; Berger et al., 1998, *Nature*, 391:240; Choe et al., 1996, *Cell*, 85:1135–1148; Deng et al., 1996, *Nature*, 381:661–666; Doranz et al., 1996, *Cell*, 85:1149–1158; Dragic et al., 1996, *Nature*, 381:667–673; and Feng et al., 1996, *Science*, 272:872–877). R5-X4 (dual-tropic) viral env proteins can, in conjunction with CD4, use either CCR5 or CXCR4 for cellular entry. The differential utilization of CCR5 and CXCR4 by HIV strains, coupled with their expression patterns in CD4 positive cells largely explains viral tropism at the level of entry.

In addition to CCR5 and CXCR4, a number of other chemokine and orphan seven transmembrane domain receptors have been shown to function as coreceptors for one or more virus strains in vitro, including CCR2b, CCR3, CCR8, CX3CR1, GPR1, GPR 15, STRL33, US28, and ChemR23 (Choe et al., 1996, *Cell* 85:1135–1148; Deng et al., 1997, *Nature* 388:296–300; Doranz et al., 1996, *Cell* 85:1149–1158; Farzan et al., 1997, *J. Exp. Med.* 186:405–411; Liao et al., 1997, *J. Exp. Med.* 195:2015–2023; Pleskoff et al., 1997, *Science* 276:1874–1878; Reeves et al., 1997, *Virology* 231:120–134; Rucker et al., 1997, *J. Virol.* 71:8999–9007). In general, these alternative coreceptors support virus infection less efficiently than either CCR5 or CXCR4. However, use of alternative coreceptors may help explain certain facets of HIV-1 tropism and pathogenesis in vivo. For example, neurologic disease is a serious and relatively frequent consequence of HIV-1 infection, with microglia being the primary targets of virus infection in the central nervous system (Bagasra et al., 1996, *AIDS*, 10:573–585; Sharer et al., 1992, *J. Neuropath. Exp. Neurol.*, 51:3–11; Wiley et al., 1986, *Proc. Natl. Acad. Sci., USA*, 83:7089–7093). Microglia express both CCR3 and CCR5 and it has been suggested that utilization of CCR3 by a virus strain may correlate with neurotropism (He et al., 1997, *Nature*, 385:645–649).

The identification of additional coreceptors for the HIV virus would provide an important tool for investigating and controlling HIV infection.

SUMMARY OF THE INVENTION

In one aspect of the invention, the invention relates to a recombinant eukaryotic cell transformed with a polynucleotide encoding an APJ polypeptide and/or a polynucleotide encoding a CD4 polypeptide, wherein the cell coexpresses APJ and CD4 polypeptides.

The invention also relates to an antibody which specifically binds to an extracellular domain of APJ, wherein the antibody inhibits HIV infection of a target cell that coexpresses APJ and CD4 polypeptides or wherein the antibody inhibits membrane fusion between a first cell coexpressing APJ and CD4 polypeptides and a second cell expressing an HIV env protein.

The invention also relates to a substantially purified peptide fragment of APJ, wherein the peptide inhibits HIV infection of a target cell that coexpresses APJ and CD4 polypeptides or wherein the peptide inhibits cell fusion between a first cell coexpressing APJ and CD4 polypeptides and a second cell expressing an HIV env protein.

In another aspect of the invention the invention relates to methods for identifying compounds that modulate the interaction between an HIV virus and an APJ receptor.

The invention also relates to a method of inhibiting HIV infection of a target cell expressing an APJ and CD4 polypeptides comprising contacting the target cell with an effective amount of an APJ binding or blocking agent.

The invention also relates to a method of treating a subject having or at risk of having an HIV infection or related disorder, comprising administering a therapeutically effective amount of an anti-APJ antibody to the subject.

BRIEF DESCRIPTION OF THE DRAWINGS

FIG. 9 is the nucleotide and deduced amino acid sequence for human APJ (O'Dowd et al., 1993, Gene 136:355–360) (SEQ ID NO: 1). The positions of the seven trans-membrane regions are as follows: transmembrane region 1 (TM 1) corresponds to amino acids 26–54; transmembrane region 2 (TM2) corresponds to amino acids 66–90; transmembrane region 3 (TM3) corresponds to amino acids 104–125; transmembrane region 4 (TM4) corresponds to amino acids 144–167; transmembrane region 5 (TM5) corresponds to amino acids 199–225; transmembrane region 6 (TM6) corresponds to amino acids 246–271; transmembrane region 7 (TM7) corresponds to amino acids 285–312. Extracellular portions of the APJ polypeptide are located in the amino terminal segment before transmembrane domain 1 (e.g. amino acids 1–25), between transmembrane domains 2 and 3 (e.g. amino acids 91–103), between transmembrane domains 4 and 5 (e.g. amino acids 168–198), and between transmembrane domains 6 and 7 (e.g. amino acids 272–284).

DETAILED DESCRIPTION OF THE INVENTION

Figure 1:
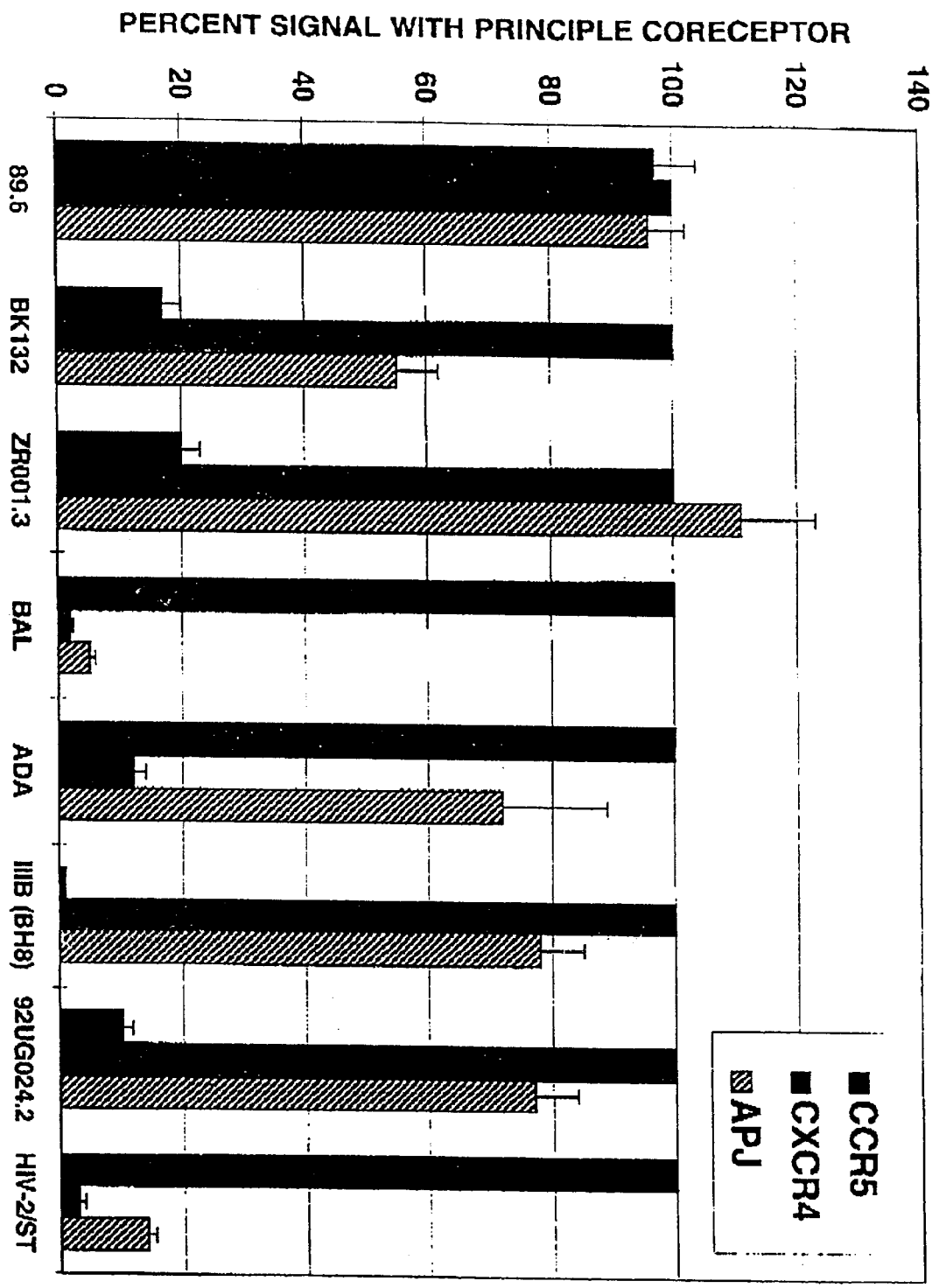
FIG. 1 is a graph showing cell-cell fusion mediated by HIV-1 or HIV-2 env proteins. All of the indicated env proteins are derived from HIV-1, with the exception of HIV-2/ST which was derived from HIV-2. QT6 cells expressing CD4, the indicated coreceptor, and luciferase under the control of the T7 promoter were mixed with cells expressing T7 polymerase and the indicated HIV-1 or HIV-2 env protein. The degree of cell-cell fusion was determined 8 hours post-mixing by measuring luciferase activity. The results were normalized by setting the extent of fusion obtained when CD4 and either CCR5 (for R5 env proteins) or CXCR4 (for X4 env proteins) were coexpressed to 100%. The extent of fusion obtained with the major HIV-1 coreceptors was generally 40 to 100 times above background levels. Error bars here and in subsequent figures represent the standard error of the mean derived from multiple independent experiments.

In accordance with this invention, it has been discovered that the orphan seven transmembrane domain receptor, APJ (O'Dowd et al., 1993, Gene 136:355–360), functions as an efficient coreceptor for a number of HIV-1 and SIV strains. APJ serves as a very efficient coreceptor for some X4 (T-tropic) and R5-X4 (dual tropic) virus strains, while two R5 (M-tropic) isolates use APJ less efficiently. APJ also served as a coreceptor for several SIV strains.

Also in accordance with this invention, the widespread expression of APJ in the human central nervous system has been discovered. The efficient use of APJ by a number of virus strains, coupled with the expression of APJ in the central nervous system, indicates that utilization of this receptor may be important in HIV neuropathogenesis.

Also in accordance with this invention, the expression of APJ in a CD4 positive T-cell line, C8166, has been discovered.

In one embodiment, the present invention relates to recombinant cell lines, the cells of which co-express APJ and CD4 polypeptides, and which contain an exogenous polynucleotide that encodes either an APJ polypeptide or a CD4 polypeptide. The present invention also relates to recombinant cell lines, the cells of which co-express APJ and CD4 polypeptides, and which contain an exogenous polynucleotide that encodes an APJ polypeptide and an exogenous polynucleotide that encodes a CD4 polypeptide. As used herein, a "CD4 polypeptide" means a mammalian CD4 polypeptide, preferably a human or a simian CD4 polypeptide, or a biologically active fragment thereof. As used herein, an "APJ polypeptide" means a mammalian APJ polypeptide, preferably a human or a simian APJ polypeptide, or a biologically active fragment thereof. Biologically active, as used herein, refers to polypeptides having an ability to specifically interact with an HIV or SIV virus and to polypeptides having at least one epitope for an antibody immunoreactive with an APJ or a CD4 polypeptide.

The invention relates not only to naturally-occurring APJ and CD4 polypeptides, but also to mutant APJ and CD4 polypeptides. For example, changes in the amino acid sequence of APJ are contemplated in the present invention. APJ can be altered by changing the DNA encoding the protein. Preferably, only conservative amino acid sequence alterations are undertaken, using amino acids that have the same or similar properties. Illustrative amino acid substitutions include the following changes: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Polynucleotide sequences of the invention include DNA, cDNA and RNA sequences which encode APJ or CD4 polypeptides. Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, APJ and CD4 polynucleotides may be subjected to site-directed mutagenesis. The polynucleotide sequence for APJ and CD4 also includes antisense sequences. The invention also includes a polynucleotide encoding an APJ polypeptide having biological activity or a CD4 polypeptide having biological activity.

Suitable cell types include, but are not limited to, cells of the following types: NIH 3T3 (Murine), Mv 1 lu (mink), BS-C-1 (African Green Monkey), human embryonic kidney (HEK) 293 cells (ATCC CRL 1573), and quail QT6 cells. Such cells are described, for example, in the Cell Line Catalog of the American Type Culture Collection (ATCC). These cells can be stably transformed or transiently transformed by a method known to the skilled artisan. See, for example, Ausubel, et al., Introduction of DNA Into Mammalian Cells, in *Current Protocols in Molecular Biology*, sections 9.5.1–9.5.6 (John Wiley & Sons, Inc. 1995). "Stable" transformation in the context of the invention means that the cells are immortal to the extent of having gone through at least 50 divisions.

Exogenous APJ or CD4 polynucleotides can be expressed using inducible or constitutive regulatory elements for expression. Commonly used constitutive or inducible promoters, for example, are known in the art. For example promoters derived from the genome of mammalian cells (e.g. metallothionein promoter) or from mammalian viruses (e.g., the retrovirus long terminal repeat, the adenovirus late promoter, the vaccinia virus 7.5K promoter) may be used. Promoters produced by recombinant DNA or synthetic techniques may also be used to provide for transcription of the exogenous APJ or CD4 polynucleotides.

The desired protein encoding sequence and operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the desired molecule may occur through the transient expression of the introduced sequence. Alternatively, permanent expression may occur through the integration of the introduced sequence into the host chromosome.

In a preferred embodiment, the introduced sequence will be incorporated into a plasmid or viral vector capable of autonomous replication in the recipient host. A wide variety of vectors may be employed for this purpose. Factors of importance in selecting a particular plasmid or viral vector include the following: the ease with which recipient cells that contain the vector may be recognized and selected from those recipient cells which do not contain the vector; the number of copies of the vector which are desired in a particular host; and whether it is desirable to "shuttle" the vector between host cells of different species.

Several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors include vaccinia virus expression vectors. A third class of vectors relies upon the integration of the desired gene sequences into the host chromosome. Cells which have stably integrated the introduced DNA into their chromosomes may be selected by also introducing one or more markers (e.g., an exogenous gene) which allow selection of host cells which contain the expression vector. The marker may provide, for example, prototrophy to an auxotrophic host or biocide resistance, e.g., antibiotic resistance or heavy metal resistance, such as copper resistance. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.*, 3:280 (1983), and others.

Once the vector or DNA sequence containing the construct has been prepared for expression, the DNA construct may be introduced (transformed) into an appropriate host. Various techniques which may be employed include, for example, protoplast fusion, calcium phosphate precipitation, electroporation, microinjection, delivery via liposomes, viral infection, or other conventional techniques.

In another embodiment, the present invention relates to transgenic animals having cells that coexpress human CD4 and APJ polypeptides. Such transgenic animals represent a model system for the study of HIV infection and the development of more effective anti-HIV therapeutics.

The term "animal", as used herein, denotes all mammalian species except human. It also includes an individual animal in all stages of development, including embryonic and fetal stages. Farm animals (pigs, goats, sheep, cows, horses, rabbits, etc.), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or by infection with a recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ cell line, therefore conferring the ability to transfer the information to offspring. If such offspring in fact possess some or all of that information they are also considered transgenic animals.

It is highly preferred that the transgenic animals of the present invention be produced by introducing into single cell embryos a polynucleotide encoding an APJ polypeptide and or a polynucleotide encoding a CD4 polypeptide, in a manner such that these polynucleotides are stably integrated into the DNA of germ line cells of the mature animal and inherited in normal mendelian fashion. Advances in technologies for embryo micromanipulation now permit introduction of exogenous polynucleotides into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired polynucleotide, and transgenic animals produced from the infected embryo.

In a most preferred method, the appropriate polynucleotides are coinjected into the pronucleus or cytoplasm of embryos, preferably at the single cell stage, and the embryos allowed to develop into mature transgenic animals. These techniques are well known. For example, reviews of standard laboratory procedures for microinjection of exogenous DNAs into mammalian (mouse, pig, rabbit, sheep, goat, cow) fertilized ova include: Hogan et al., *Manipulating The Mouse Embryo* (Cold Spring Harbor Press 1986); Krimpenfort et al., *Bio/Technology* 9:86 (1991); Palmiter et al., *Cell* 41:343 (1985); Kraemer et al., *Genetic Manipulation of The*

*Early Mammalian Embryo* (Cold Spring Harbor Laboratory Press 1985); Hammer et al., *Nature* 315:680 (1985); Purcel et al., *Science* 244: 1281 (1986); Wagner et al., U.S. Pat. No. 5,175,385; Krimpenfort et al., U.S. Pat. No. 5,175,384, the respective contents of which are herein incorporated by reference.

The polynucleotide that encodes APJ or CD4 can be fused in proper reading frame under the transcriptional and translational control of a vector to produce a genetic construct that is then amplified, for example, by preparation in a bacterial vector, according to conventional methods. See, for example, the standard work: Sambrook et al., *Molecular Cloning: a Laboratory Manual* (Cold Spring Harbor Press 1989), the contents of which are herein incorporated by reference. The amplified construct is thereafter excised from the vector and purified for use in producing transgenic animals.

Production of transgenic animals containing the gene for human CD4 have been described. See Snyder et al., *Mol. Reprod. & Devel.* 40:419–428 (1995); Dunn et al., *J Gen. Virology* 76:1327–1336 (1995), the contents of which are incorporated by reference.

In another embodiment, the present invention relates to antibodies that bind APJ and that inhibit HIV entry into a CD4-positive target cell or that inhibit cell-cell fusion between a first cell type that expresses CD4 and APJ polypeptides and a second cell type that expresses the env protein. As used herein, an env protein means any env protein derived from an HIV virus, either HIV-1 or HIV-2, or derived from an SIV virus. Expression of an env protein by a cell will typically result in the expression of the gp120 moiety of the env protein on the cell surface. Antibodies of the invention may also inhibit gp120 binding to APJ. Such antibodies could represent research and diagnostic tools in the study of HIV infection and the development of more effective anti-HIV therapeutics. In addition, pharmaceutical compositions comprising antibodies against APJ may represent effective anti-HIV therapeutics.

An antibody suitable for blocking env-mediated cell-cell fusion, HIV entry into a CD4 positive cell, or gp120 binding to APJ is specific for at least one portion of an extracellular region of the APJ polypeptide, e.g. the first extracellular region (amino acids 1–25), the second extracellular region (amino acids 91–103), the third extracellular region (amino acids 168–198), or the fourth extracellular region (amino acids 272–284), as shown in FIG. 9. Preferred antibodies are those which recognize an epitope comprising a portion of either the first extracellular region or the second extracellular region. Particularly preferred antibodies are those which recognize an epitope comprising the Asn-Tyr-Tyr-Gly (SEQ ID NO: 3) amino acid sequence contained within the first extracellular region.

Anti-APJ antibodies of the invention include polyclonal antibodies, monoclonal antibodies, and fragments of polyclonal and monoclonal antibodies. The preparation of polyclonal antibodies is well-known to those skilled in the art. See, for example, Green et al., Production of Polyclonal Antisera, in *Immunochemical Protocols* (Manson, ed.), pages 1–5 (Humana Press 1992); Coligan et al., Production of Polyclonal Antisera in Rabbits, Rats, Mice and Hamsters, in *Current Protocols in Immunology,* section 2.4.1 (1992), which are hereby incorporated by reference.

The preparation of monoclonal antibodies likewise is conventional. See, for example, Kohler & Milstein, *Nature* 256:495 (1975); Coligan et al., *Current Protocols in Immunology,* sections 2.5.1–2.6.7; and Harlow et al., *Antibodies: A Laboratory Manual,* page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatograhy, antigen affinity purification and ion-exchange chromatography. See, e.g., Coligan et al., *Current Protocols in Immunology,* sections 2.7.1–2.7.12 and sections 2.9.1–2.9.3; Barnes et al., Purification of lmmunoglobulin G (IgG), in *Methods in Molecular Biology,* Vol. 10, pages 79–104 (Humana Press 1992).

Methods of in vitro and in vivo multiplication of monoclonal antibodies are well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for anti-APJ antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J Cancer* 46:310 (1990), which are hereby incorporated by reference.

Alternatively, a therapeutically or diagnostically useful anti-APJ antibody may be derived from a "humanized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. USA* 86:3833 (1989), which is hereby incorporated in its entirety by reference. Techniques for producing humanized monoclonal antibodies are described, for example, by Jones et al., *Nature* 321:522 (1986); Riechmann et al., *Nature* 332:323

(1988); Verhoyen et al., *Science* 239:1534 (1988); Carter et al., *Proc. Natl. Acad. Sci. USA* 89:4285 (1992); Sandhu, *Crit. Rev. Biotech.* 12:437 (1992); and Singer et al., *J. Immunol.* 150:2844 (1933), which are hereby incorporated by reference.

Antibodies of the invention may also be derived from human antibody fragments isolated from a combinatorial immunoglobulin library. See, for example, Barbas et al., *Methods: A Companion to Methods in Enzymology*, Vol. 2, page 119 (1991); Winter et al., *Ann. Rev. Immunol.* 12:433 (1994), which are hereby incorporated by reference. Cloning and expression vectors that are useful for producing a human immunoglobulin phage library can be obtained, for example, from Stratagene Cloning Systems (La Jolla, Calif.).

In addition, antibodies of the present invention may be derived from a human monoclonal antibody. Such antibodies are obtained from transgenic mice that have been "engineered" to produce specific human antibodies in response to an antigenic challenge. In this technique, elements of the human heavy and light chain loci are introduced into strains of mice derived from embryonic cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., *Arch. Biochem. Biophys.* 89:230 (1960); Porter, *Biochem. J.* 73:119 (1959); Edelman et al., *Methods in Enzymology*, Vol. 1, page 422 (Academic Press 1967); and Coligan et al., *Current Protocols in Immunology*, sections 2.8.1–2.8.10 and 2.10.1–2.10.4.

Other methods of cleaving antibodies, such as separation of heavy and light chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Natl. Acad. Sci. USA* 69:2659 (1972). Alternatively, the variable chains can be linked by an intermolecular disulfide bond or cross-linked by chemicals such as glutaraldehyde. See, e.g., Sandhu, *Crit. Rev. Biotech.* 12:437 (1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology*, Vol. 2, page 97 (1991); Bird et al., *Science* 242:423–426 (1988); Ladner et al., U.S. Pat. No. 4,946,778; Pack et al., *Bio/Technology* 11: 1271–77 (1993); and Sandhu, *Crit. Rev. Biotech.* 12:437 (1992).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology*, Vol. 2, page 106 (1991).

Antibodies that bind to the CXCR4 chemokine receptor, another HIV coreceptor, have been shown to block fusion of HIV strains that use CXCR4 receptor for infection (Feng, et al., *Science* 272:872 (1996); Endres, et al., *Cell* 87:745 (1996)).

In another embodiment, the present invention relates to "APJ variants". An APJ variant, as used herein, means a molecule that simulates at least part of the structure of APJ and that inhibits HIV entry into a target cell expressing CD4 and APJ polypeptides or that inhibits cell-cell fusion between a first cell type that expresses CD4 and APJ polypeptides and a second cell type that expresses the env protein. The env protein of certain HIV isolates may participate in HIV infectivity by binding to APJ at the cell surface. While not wishing to be bound by a particular theory of the invention, the inventors believe that APJ variants may interfere in HIV infectivity by competing with APJ in binding to env.

In one embodiment, the present invention relates to APJ variants that are peptides and peptide derivatives that have fewer amino acid residues than APJ. Such peptides and peptide derivatives could represent research and diagnostic tools in the study of HIV infection and the development of more effective anti-HIV therapeutics.

Peptides and peptide derivatives of APJ, according to the present invention, include those which correspond to the extracellular regions of APJ, e.g. the first extracellular region (amino acids 1–25), the second extracellular region (amino acids 91–103), the third extracellular region (amino acids 168–198), or the fourth extracellular region (amino acids 272–284), as shown in FIG. 9. Peptides that correspond to the extracellular loops of another HIV coreceptor, the CCR5 coreceptor, have previously been shown to inhibit fusion between cells expressing the HIV-1 env and murine cells co-expressing CD4 and CCR5 (Combadiere et al., PCT/US97/09586, publication number WO 97/45543). Preferred peptides and peptide derivatives are those which correspond to a portion of either the first extracellular region or the second extracellular region. Particularly preferred peptides or peptide derivatives are those which comprise the Asn-Tyr-Tyr-Gly (SEQ ID NO: 3) amino acid sequence contained within the first extracellular region.

APJ variants useful for the present invention comprise analogs, homologs, muteins and mimetics of APJ. The variants can be generated directly from APJ itself by chemical modification, by proteolytic enzyme digestion, or by combinations thereof. Additionally, genetic engineering techniques, as well as methods of synthesizing polypeptides directly from amino acid sequences, can also be employed.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods (described in Merrifield, *J. Am. Chem. Soc.*, 85:2149 (1962) and Stewart and Young, *Solid Phase Peptide Synthesis* (Freeman, San Francisco, 1969) pp. 27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. The crude material can normally be purified by standard techniques such as, for example, by gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by solid phase Edman degradation analysis.

Alternatively, peptides can be produced by recombinant methods which are well known to those of skill in the art.

The term "substantially purified", as used herein, refers to a molecule, such as a peptide that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify APJ peptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC), and amino-terminal amino acid sequence analysis.

Non-peptide compounds that mimic the binding and function of APJ ("mimetics",) can be produced by the approach outlined in Saragovi et al., *Science* 253:792–95 (1991). Mimetics are molecules which mimic elements of protein secondary structure. See, for example, Johnson et al., Peptide Turn Mimetics, in *Biotechnology and Pharmacy*, Pezzuto et al., Eds., (Chapman and Hall, New York 1993). The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of APJ itself.

Longer peptides can be produced by the "native chemical" ligation technique which links together peptides (Dawson, et al., *Science* 266:776 (1994)). Variants can be created by recombinant techniques employing genomic or cDNA cloning methods. Site-specific and region-directed mutagenesis techniques can be employed. See *Current Protocols in Molecular Biology*, Vol. 1, ch. 8 (Ausubel et al. eds., J. Wiley & Sons 1989 & Supp. 1990–93); *Protein Engineering* (Oxender & Fox eds., A. Liss, Inc. 1987). In addition, linker-scanning and PCR-mediated techniques can be employed for mutagenesis. See PCR Technology (Erlich ed., Stockton Press 1989); *Current Protocols in Molecular Biology*, Vols. 1 & 2, supra. Protein sequencing, structure and modeling approaches for use with any of the above techniques are disclosed in *Protein Engineering*, loc. cit., and *Current Protocols in Molecular Biology*, Vol. 1 & 2, supra.

If the compounds described above are employed, the skilled artisan can routinely ensure that such compounds are amenable for use with the present invention in view of the cell-cell fusion assay systems and the infectivity assay systems described herein.

The invention also includes various pharmaceutical compositions that inhibit HIV entry into a target cell expressing CD4 and APJ polypeptides. The pharmaceutical compositions according to the invention are prepared by bringing an APJ variant or an antibody against APJ, according to the present invention, into a form suitable for administration to a subject using carriers, excipients and additives or auxiliaries. Frequently used carriers or auxiliaries include magnesium carbonate, titanium dioxide, lactose, mannitol and other sugars, talc, milk, protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial agents, anti-oxidants, chelating agents and inert gases. Other pharmaceutically acceptable carriers include aqueous solutions, non toxic excipients, including salts, preservatives, buffers and the like, as described for instance, in Remington's Pharmaceutical Sciences, 15th ed. Easton: Mack Publishing Co., 1405–1412, 1461–1487 (1975), the contents of which are hereby incorporated by reference. The pH and exact concentration of the various components of the pharmaceutical composition are adjusted according to routine skills in the art. See *Goodman and Gilman's The Pharmacological Basis for Therapeutics* (7th ed.).

In another embodiment, the invention relates to a method of inhibiting HIV entry into a target cell. This method involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human. For example, neuropathy has been observed in the brains of newborn infants that are born to HIV-1 seropositive mothers (Kolson et al., 1998, *Adv. Virus Res.* 50:1–47). Therefore, a particularly preferred method is a method of treating a fetal subject having or at risk of having an HIV infection by the administration of an anti-APJ antibody or an APJ peptide fragment. The anti-APJ antibody and the APJ peptide fragment are preferably administered to the fetal subject via administration to the mother.

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally, or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science* 249:1527–1533 (1990), which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al. (eds.) (1990) *Goodman and Gilman's: The Pharmacological Bases of Therapeutics*, 8th ed., Pergamon Press; and *Remington's Pharmaceutical Sciences*, 17th ed. (1990), Mack Publishing Co., Easton, Pa., each of which is herein incorporated by reference.

Another preferred embodiment of this invention is in the diagnosis of susceptibility to HWV infection. Nucleotide sequences encoding the APJ receptor and antibodies to the APJ receptor can be particularly useful for diagnosis of susceptibility to infection where higher levels of the receptors indicate an increased risk for HIV infection. For example, higher levels of the APJ receptor in tissues of the central nervous system may indicate an increased risk of neuropathogenesis associated with HIV infection.

Using any suitable technique known in the art, such as Northern blotting, quantitative PCR, etc., the nucleotide sequences of the receptor or fragments thereof can be used to measure levels of APJ RNA expression.

Alternatively, antibodies to APJ can be used in standard techniques such as Western blotting to detect the presence of cells expressing the APJ receptor and in standard techniques, e.g. FACS or ELISA, to quantify the level of expression. For any biological tissue sample, a level of APJ expression that is greater than a reference level is indicative of increased susceptibility to HIV infection. A reference level may be established by surveying a large population of individuals.

In a preferred embodiments, the invention relates to methods for screening a compound ("test compound",) for anti-HIV pharmacological activity.

In one embodiment, a cell fusion assay is used to screen for a compound with anti-HIV pharmacological activity. In the cell fusion assay, one type of eukaryotic cell that coexpresses APJ and CD4 polypeptides is incubated with a second type of eukaryotic cell that expresses an HIV envelope protein ("env",). Fusion between the two different cell types is then monitored. The test compound is added to the incubation solution before or after mixing of the cells and its effect on the fusion rate of cells is determined by any number of means, including through morphological observation or through the use of an indicator system in conjunction with the cell fusion assay. Indicator systems useful in conjunction with a cell fusion assay can be any combination of elements wherein a detectable signal is produced when a first component in a first cell is brought into contact with a second component in a second cell by cell-cell fusion. For example, the first component may be a gene encoding a polymerase such as T7 polymerase and the second component may be a gene encoding a reporter molecule which is under the control of the T7 promoter, such as a luciferase gene. For example, a system that results in the production of an active β-galactosidase reporter molecule upon cell fusion is also contemplated.

In another embodiment, an infectivity assay is used to screen for a compound with anti-HIV pharmacological activity. In an infectivity assay, a target eukaryotic cell that expresses APJ and CD4 polypeptides is incubated with a test virus expressing an HIV env protein. Infection of the target cell with the test virus is then monitored. The test compound is added to the incubation solution before or after mixing of the target cells with the test virus, and the effect of the compound on the infection rate of target cells is determined by any number of means. The test virus may be a reporter virus in which the env protein is pseudotyped onto a reporter virus background. Alternatively, the test virus may be an intact HIV virus. Infectivity is generally monitored by use of an indicator system in conjunction with the infectivity assay. Any number of indicator systems may be used, and indicator systems which produce a detectable signal upon infection are preferred. For example, the reporter virus may be constructed with a gene encoding a reporter molecule such as luciferase and β-galactosidase, which is expressed when the reporter virus infects the target cell. As another example, the target cell may contain a gene encoding a reporter molecule under the control of the LTR promoter, thereby resulting in expression of the reporter molecule upon infection of the target cell with the HIV virus. Alternatively, viral infection may be monitored through the use of a PCR to detect viral sequences within the infected cell.

The cell fusion assay and the HIV infectivity assay can be used to determine the functional ability of APJ to confer env-mediated fusion competence to a diverse range of CD4 positive cell types (either recombinantly produced or naturally occurring), including but not limited to NIH 3T3 (murine), BS-C-1 (African green monkey), HEK 293 (human), Mv1Lu (mink), U-87 MG glioblastoma, SCL1, and QT6 (quail). HIV strains that may be used in conjunction with the assays, or as sources for env protein genes to be used in conjunction with the assays, include M-tropic, T-tropic and dual tropic strains. For example, the 89.6 dual tropic strain, the JRFL M-tropic strain, and the IIIB T-tropic HIV-1 strains may be employed (Matthews et al., 1986, *Proc. Natl. Acad. Sci. USA* 83:9709–9713; Colhman et al., 1992, *J. Virol.* 66:7517–7521; Gartner et al., 1986, *Science* 233:215–219). Additionally, selected primary isolates may also be employed.

Variations of drug screening methods are known to the artisan of average skill in this field. Consequently, the cell fusion assay and the HIV infectivity assay can be used in a wide variety of formats to exploit the properties of the APJ receptor to screen for drugs that are effective against HIV.

Another embodiment of the invention employs the use of antisense technology as a specific and potent means of inhibiting HIV infection of cells that contain APJ, for example, by decreasing the amount of APJ expression in a cell. Antisense polynucleotides in context of the present invention includes both short sequences of DNA known as oligonucleotides of usually 10–50 bases in length as well as longer sequences of DNA that may exceed the length of the APJ gene sequence itself. Antisense polynucleotides useful for the present invention are complementary to specific regions of a corresponding target mRNA. Hybridization of antisense polynucleotides to their target transcripts can be highly specific as a result of complementary base pairing. The capability of antisense polynucleotides to hybridize is affected by such parameters as length, chemical modification and secondary structure of the transcript which can influence polynucleotide access to the target site. See Stein et al., *Cancer Research* 48:2659 (1988). An antisense polynucleotide can be introduced to a cell by introducing a DNA segment that codes for the polynucleotide into the cell such that the polynucleotide is made inside the cell. An antisense polynucleotide can also be introduced to a cell by adding the polynucleotide to the environment of the cell such that the cell can take up the polynucleotide directly. The latter route is preferred for the shorter polynucleotides of up to about 20 bases in length.

In selecting the preferred length for a given polynucleotide, a balance must be struck to gain the most favorable characteristics. Shorter polynucleotides such as 10-mers to 15-mers, while offering higher cell penetration, have lower gene specificity. In contrast, while longer polynucleotides of 20–30 bases offer better specificity, they show decreased uptake kinetics into cells. See Stein et al., *Phosphorothioate Oligodeoxynucleotide Analogues in Oligodeoxynucleotides-Antisense Inhibitors of Gene Expression* (Cohen, ed., McMillan Press, London 1988). Accessibility to mRNA target sequences also is of importance and, therefore, loop-forming regions in targeted mRNAs offer promising targets.

In this disclosure, the term "polynucleotide" encompasses both oligomeric nucleic acid moieties of the type found in nature, such as the deoxyribonucleotide and ribonucleotide structures of DNA and RNA, and man-made analogues which are capable of binding to nucleic acids found in nature. The polynucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind naturally occurring DNA and RNA structures. Such polynucleotides may be prespared by methods well well-known in the art, for instance using commercially available machines and reagents available from Perkin-Elmer/Applied Biosystems (Foster City, Calif.).

Phosphodiester-linked polynucleotides are particularly susceptible to the action of nucleases in serum or inside cells, and therefore in a preferred embodiment the polynucleotides of the present invention are phosphorothioate or methyl phosphonate-linked analogues, which have been shown to be nuclease resistant. Persons of ordinary skill in this art will be able to select other linkages for use in the invention. These modifications also may be designed to improve the cellular uptake and stability of the polynucleotides.

In another embodiment of the invention, the antisense polynucleotide is an RNA molecule produced by introducing an expression construct into the target cell. The RNA molecule thus produced is chosen to have the capability to hybridize to APJ mRNA. Such molecules that have this capability can inhibit translation of the APJ mRNA and thereby inhibit the ability of HIV to infect cells that contain the RNA molecule.

The polynucleotides which have the capability to hybridize with mRNA targets can inhibit expression of corresponding gene products by multiple mechanisms. In "translation arrest", the interaction of polynucleotides with target mRNA blocks the action of the ribosomal complex and, hence, prevents translation of the messenger RNA into protein. Haeuptle et al., *Nucl. Acids. Res.* 14:1427 (1986). In the case of phosphodiester or phosphorothioate DNA polynucleotides, intracellular RNase H can digest the targeted RNA sequence once it has hybridized to the DNA oligomer. Walder and Walder, *Proc. Natl. Acad. Sci. USA* 85:5011 (1988). As a further mechanism of action, in "transcription arrest" it appears that some polynucleotides can form "triplex," or triple-helical structures with double stranded genomic DNA containing the gene of interest, thus interfering with transcription by RNA polymerase. Giovannangeli et al., *Proc. Natl. Acad. Sci.* 90:10013 (1993); Ebbinghaus et al., *J. Clin. Invest.* 92:2433 (1993).

In one preferred embodiment, APJ polynucleotides are synthesized according to standard methodology. Phosphorothioate modified DNA polynucleotides typically are synthesized on automated DNA synthesizers available from a variety of manufacturers. These instruments are capable of synthesizing nanomole amounts of polynucleotides as long as 100 nucleotides. Shorter polynucleotides synthesized by modem instruments may be purified by polyacrylamide gel electrophoresis or reverse phase chromatography. See Sambrook et al., *Molecular Cloning: A Laboratory Manual,* Vol. 2, Chapter 11, Cold Spring Harbor Laboratory Press, Cold Spring Harbor, N.Y. (1989).

Alternatively, a APJ polynucleotide in the form of antisense RNA may be introduced to a cell by its expression within the cell from a standard DNA expression vector. APJ DNA antisense sequences can be cloned from standard plasmids into expression vectors, which expression vectors have characteristics permitting higher levels of, or more efficient expression of the resident polynucleotides. At a minimum, these constructs require a prokaryotic or eukaryotic promoter sequence which initiates transcription of the inserted DNA sequences. A preferred expression vector is one where the expression is inducible to high levels. This is accomplished by the addition of a regulatory region which provides increased transcription of downstream sequences in the appropriate host cell. See Sambrook et al., *Molecular Cloning: A Laboratory Manual* Vol. 3, Chapter 16, Cold Spring Harbor Laboratory Press, Cold Spring Harbor, N.Y. (1989).

For example, APJ antisense expression vectors can be constructed using the polymerase chain reaction (PCR) to amplify appropriate fragments from single-stranded cDNA of a plasmid such as pRc in which APJ cDNA has been incorporated. Fang et al., *J. Biol. Chem.* 267:25889–25897 (1992). Polynucleotide synthesis and purification techniques are described in Sambrook et al. and Ausubel et al. (eds.), *Current Protocols in Molecular Biology* (Wiley Interscience 1987) (hereafter "Ausubel",), respectively. The PCR procedure is performed via well-known methodology. See, for example, Ausubel, and Bangharn, The Polymerase Chain Reaction: Getting Started, in *Protocols in Human Molecular Genetics* (Humana Press 1991). Moreover, PCR kits can be purchased from companies such as Stratagene Cloning Systems (La Jolla, Calif.) and Invitrogen (San Diego, Calif.).

The products of PCR are subdloned into cloning vectors. In this context, a "cloning vector" is a DNA molecule, such as a plasmid, cosmid or bacteriophage, that can replicate autonomously in a host prokaryotic cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Suitable cloning vectors are described by Sambrook et al., Ausubel, and Brown (ed.), *Molecular Biology Labfax* (Academic Press 1991). Cloning vectors can be obtained, for example, from GIBCO/BRL (Gaitherburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

Preferably, the PCR products are ligated into a "TA" cloning vector. Methods for generating PCR products with a thymidine or adenine overhang are well-known to those of skill in the art. See, for example, Ausubel at pages 15.7.1–15.7.6. Moreover, kits for performing TA cloning can be purchased from companies such as Invitrogen (San Diego, Calif.).

Cloned antisense fragments are amplified by transforming competent bacterial cells with a cloning vector and growing the bacterial host cells in the presence of the appropriate antibiotic. See, for example, Sambrook et al., and Ausubel. PCR is then used to screen bacterial host cells for APJ antisense orientation clones. The use of PCR for bacterial host cells is described, for example, by Hoffmnan et al., Sequencing DNA Amplified Directly from a Bacterial Colony, in *PCR Protocols: Methods And Applications*, White (ed.), pages 205–210 (Humana Press 1993), and by Cooper et al., PCR-Based Full-Length cDNA Cloning Utilizing the Universal-Adaptor/Specific DOS Primer-Pair Strategy, Id. at pages 305–316.

Cloned antisense fragments are cleaved from the cloning vector and inserted into an expression vector. For example, HindIII and XbaI can be used to cleave the antisense fragment from TA cloning vector pCRm™-II (Invitrogen; San Diego, Calif.). Suitable expression vectors typically contain (1) prokaryotic DNA elements coding for a bacterial origin of replication and an antibiotic resistance marker to provide for the amplification and selection of the expression vector in a bacterial host; (2) DNA elements that control initiation of transcription, such as a promoter; and (3) DNA elements that control the processing of transcripts, such as a transcription termination/polyadenylation sequence.

For a mammalian host, the transcriptional and translational regulatory signals preferably are derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Mol. Appl. Genes.* 1:273 (1982)); the TK promoter of Herpes virus (McKnight, *Cell* 31:355 (1982)); the SV40 early promoter (Benoist et al., *Nature* 290:304 (1981); the Rous sarcoma virus promoter (Gorman et al., *Proc. Nat'l. Acad. Sci. USA,* 79:6777 (1982)); and the cytomegalovirus promoter (Foecking et al., *Gene* 45:101 (1980)).

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10:4529 (1990); Kaufinan et al., *Nuci. Acids Res.* 19:44–85 (1991).

A vector for introducing at least one antisense polynucleotide into a cell by expression from a DNA is the vector pRc/CMV (Invitrogen, San Diego, Calif.), which provides a high level of constitutive transcription from mammalian enhancer-promoter sequences. Cloned APJ antisense vectors are amplified in bacterial host cells, isolated from the cells, and analyzed as described above.

Another possible method by which antisense sequences may be exploited is via gene therapy. Virus-like vectors, usually derived from retroviruses, may prove useful as vehicles for the importation and expression of antisense constructs in human cells. Generally, such vectors are non-replicative in vivo, precluding any unintended infection of non-target cells. In such cases, helper cell lines are provided which supply the missing replicative functions in vivo, thereby permitting amplification and packaging of the antisense vector. A further precaution against accidental infection of non-target calls involves the use of target cell-specific regulatory sequences. When under the control of such sequences, antisense constructs would not be expressed in normal tissues.

Two prior studies have explored the feasibility of using antisense polynucleotides to inhibit the expression of a heparin binding growth factor. Kouhara et al., *Oncogene* 9:455–462 (1994); Morrision, *J. Biol. Chem.* 266:728 (1991). Kouhara et al. showed that androgen-dependent growth of mouse mammary carcinoma cells (SC-3) is mediated through induction of androgen-induced, heparin binding growth factor (AIGF). An antisense 15-mer corresponding to the translation initiation site of AIGF was measured for its ability to interfere with androgen-induction of SC-3 cells. At concentrations of 5 μM, the antisense polynucleotide-effectively inhibited DNA synthesis. Morrision showed that antisense polynucleotides targeted against basic fibroblast growth factor can inhibit growth of astrocytes in culture. Thus, the general feasibility of targeting an individual gene product in a mammalian cell has been established.

Antisense polynucleotides according to the present invention are derived from any portion of the open reading frame of the APJ cDNA. Preferably, mRNA sequences (i) surrounding the translation initiation site and (ii) forming loop structures are targeted. Based upon the size of the human genome, statistical studies show that a DNA segment approximately 14–15 base pairs long will have a unique sequence in the genome. To ensure specificity of targeting APJ RNA, therefore, it is preferred that the antisense polynucleotides are at least 15 nucleotides in length. Thus, the shortest polynucleotides contemplated by the present invention encompass nucleotides corresponding to positions 1–14, 1–15, 1–16, 1–17, 1–18, 1–19, 2–16, 3–17, etc. of the APJ cDNA sequence. Position 1 refers to the first nucleotide of the APJ coding region.

Not every antisense polynucleotide will provide a sufficient degree of inhibition or a sufficient level of specificity for the APJ target. Thus, it will be necessary to screen polynucleotides to determine which have the proper antisense characteristics. A preferred method to assay for a useful antisense polynucleotide is the inhibition of cell fusion between (1) cells that contain CD4 and APJ; and (2) cells that contain env.

Administration of an antisense polynucleotide to a subject, either as a naked, synthetic polynucleotide or as part of an expression vector, can be effected via any common route (oral, nasal, buccal, rectal, vaginal, or topical), or by subcutaneous, intramuscular, interperitoneal, or intravenous injection. Pharmaceutical compositions of the present invention, however, are advantageously administered in the form of injectable compositions. A typical composition for such purpose comprises a pharmaceutically acceptable solvent or diluent and other suitable, physiologic compounds. For instance, the composition may contain polynucleotide and about 10 mg of human serum albumin per milliliter of a phosphate buffer containing NaCl.

As much as 700 milligrams of antisense polynucleotide has been administered intravenously to a patient over a course of 10 days (i.e., 0.05 mg/kg/hour) without signs of toxicity. Sterling, "Systemic Antisense Treatment Reported," *Genetic Engineering News* 12:1, 28 (1992).

Other pharmaceutically acceptable excipients include non-aqueous or aqueous solutions and non-toxic compositions including salts, preservatives, buffers and the like. Examples of non-aqueous solutions are propylene glycol, polyethylene glycol, vegetable oil and injectable organic esters such as ethyloleate. Aqueous solutions include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. A preferred pharmaceutical composition for topical administration is a dermal cream or transdermal patch.

Antisense polynucleotides or their expression vectors may be administered by injection as an oily suspension. Suitable lipophilic solvents or vehicles include fatty oils, such as sesame oil, or synthetic fatty acid esters, such as ethyl oleate or triglycerides. Moreover, antisense polynucleotides or vectors may be combined with a lipophilic carrier such as any one of a number of sterols including cholesterol, cholate and deoxycholic acid. A preferred sterol is cholesterol. Aqueous injection suspensions may contain substances which increase the viscosity of the suspension include, for example, sodium carboxymethyl cellulose, sorbitol, and/or dextran. Optionally, the suspension also contains stabilizers.

An alternative formulation for the administration of antisense APJ polynucleotides involves liposomes. Lipsome encapsulation provides an alternative formulation for the administration of antisense APJ polynucleotides and expression vectors. Liposomes are microscopic vesicles that consist of one or more lipid bilayers surrounding aqueous compartments. See, generally, Bakker-Woudenberg et al., *Eur. J. Clin. Microbiol. Infect. Dis.* 12 (Suppl. 1): S61 (1993), and Kim, *Drugs* 46:618 (1993). Lipsomes are similar in composition to cellular membranes and as a result, liposomes can be administered safety and are biodegradable. Depending on the method of preparation, liposomes may be unilamellar or multilamellar, and liposomes can vary in size with diameters ranging from 0.01 $\mu$m to greater than 10 $\mu$m. A variety of agents can be encapsulated in liposomes: hydrophobic agents partition in the bilayers and hydrophilic agents partition within the inner aqueous space(s). See, for example, Machy et al., *Liposomes in Cell Biology And Pharmacology* (John Libby 1987), and Ostro et al., *American J. Hosp. Pharm.* 46:1576 (1989). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell then slowly release the encapsulated agent. Alternatively, an absorbed liposome may be endocytosed by cells that are phagocytic. Endocytosis is followed by intralysosomal degradation of liposomal lipids and release of the encapsulated agents. Scherphof et al., *Ann. N.Y. Acad. Sci.* 446:368 (1985).

After intravenous administration, conventional liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802:428 (1984). In addition, incorporation of glycolipid- or polyethelene glycol-derivatised phospholipids into liposome membranes has been shown to result in a significantly reduced uptake by the reticuloendothelial system. Allen et al., *Biochim. Biophys. Acta.* 1068:133 (1991); Allen et al., *Biochim. Biophys. Acta* 1150:9 (1993). These Stealth® liposomes have an increased circulation time and an improved targeting to tumors in animals. Woodle et al., *Proc. Ameri. Assoc. Cancer Res.* 33:2672 (1992); Gregoriadis et al., *Drugs* 45:15 (1993).

Antisense polynucleotides and expression vectors can be encapsulated within liposomes using standard techniques. A variety of different liposome compositions and methods for synthesis are known to those of skill in the art. See, for example, U.S. Pat. Nos. 4,844,904, 5,000,959, 4,863,740, and 4,975,282, all of which are hereby incorporated by reference.

Liposomes can be prepared for targeting to particular cells or organs by varying phospholipid composition or by inserting receptors or ligands into the liposomes. For instance, antibodies specific to tumors associated with antigens may be incorporated into liposomes, together with antisense polynucleotides or expression vectors, to target the liposome more effectively to the tumor cells. See, for example, Zelphati et al., *Antisense Research and Development* 3:323–338 (1993), describing the use "immunoliposomes" containing antisense polynucleotides for human therapy.

In general, the dosage of administered liposome-encapsulated antisense polynucleotides and vectors will vary depending upon such factors as the patient's age, weight, height, sex, general medical condition and previous medical history. Dose ranges for particular formulations can be determined by using a suitable animal model.

The above approaches can also be used not only with antisense nucleic acids, but also with ribozymes, or triplex agents to block transcription or translation of a specific APJ mRNA, either by masking that mRNA with an antisense nucleic acid or triplex agent, or by cleaving it with a ribozyme.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hassellhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

Without further elaboration, it is believed that one skilled in the art can, using the preceding description, utilize the present invention to its fullest extent. The following examples are to be considered illustrative and thus are limiting to the remainder of the disclosure.

EXAMPLES

Example 1

A cell-cell Fussion Assay to Determine Whether APJ Could Function as a Coreceptor for HIV-1 or SIV A cell-cell fusion assay was employed to determine whether APJ could function as a coreceptor for HIV-1 or SIV. This assay has been described in detail in Nussbaum et al., 1994, *J. Virol.*, 68:5411–5422 and in Rucker et al., 1997, *Meth. Enzymol.*, 288:118–133. Effector cells were prepared by infecting quail QT6 cells with a recombinant vaccinia virus encoding T7 polymerase (vTF1.1) and then either transfecting the cells with a plasmid bearing the envelope gene of interest under the control of the T7 promoter or introducing the env constructs via recombinant vaccinia virus. Env constructs SIVmac251, SIVmac239, SIVmac316, SIVmac316mut, DH12, RF, BK132, ADA, JR-FL, IIIB and HIV-2 ST were introduced into effector cells via recombinant vaccinia virus rather than by transfection. QT6 target cells were prepared by transient transfection with plasmids encoding CD4, the coreceptor of interest under the control of the CMV promoter, and luciferase under the control of the T7 promoter. Effector and target cells were mixed the day after transfection and cell-cell fusion was quantified by measuring luciferase activity in cell lysates 7–8 hours following mixing.

In this assay, cell-cell fusion results in cytoplasmic mixing and luciferase production, which can be easily quantified. As shown in FIG. 1, co-expression of either the CCR5 or the CXCR4 coreceptor with CD4 resulted in efficient fusion by R5 and X4 Env proteins, respectively. R5–X4 env proteins such as HIV-1 89.6 mediated fusion with cells bearing either the CCR5 or the CXCR4 coreceptor. Fusion was not observed when CD4 was expressed alone. When APJ was co-expressed with CD4 in QT6 cells, cell-cell fusion was mediated by the R5–X4 Env protein 89.6 and by several X4 env proteins at levels $\geq 70\%$ of that observed with CXCR4 (FIG. 1). For one primary X4 env protein, ZR001.3, fusion with cells expressing APJ was more efficient than with CXCR4. A majority of R5 env proteins mediated fusion with APJ expressing cells, but only at very low levels relative to that observed with CCR5 (FIG. 1 and Table 1). However, ADA and the primary isolate TH 22-4 exhibited fusion mediated by APJ at roughly half the level observed when CCR5 served as the viral coreceptor. The HIV-2 ST env protein also mediated very inefficient fusion with cells expressing both CD4 and APJ. The ability of APJ to support fusion for some X4 and R5–X4 viral env proteins nearly as efficiently as the major coreceptors is notable, since most other alternative HIV-1 coreceptors typically support cell-cell fusion much less efficiently than CCR5 or CXCR4.

Figure 2:
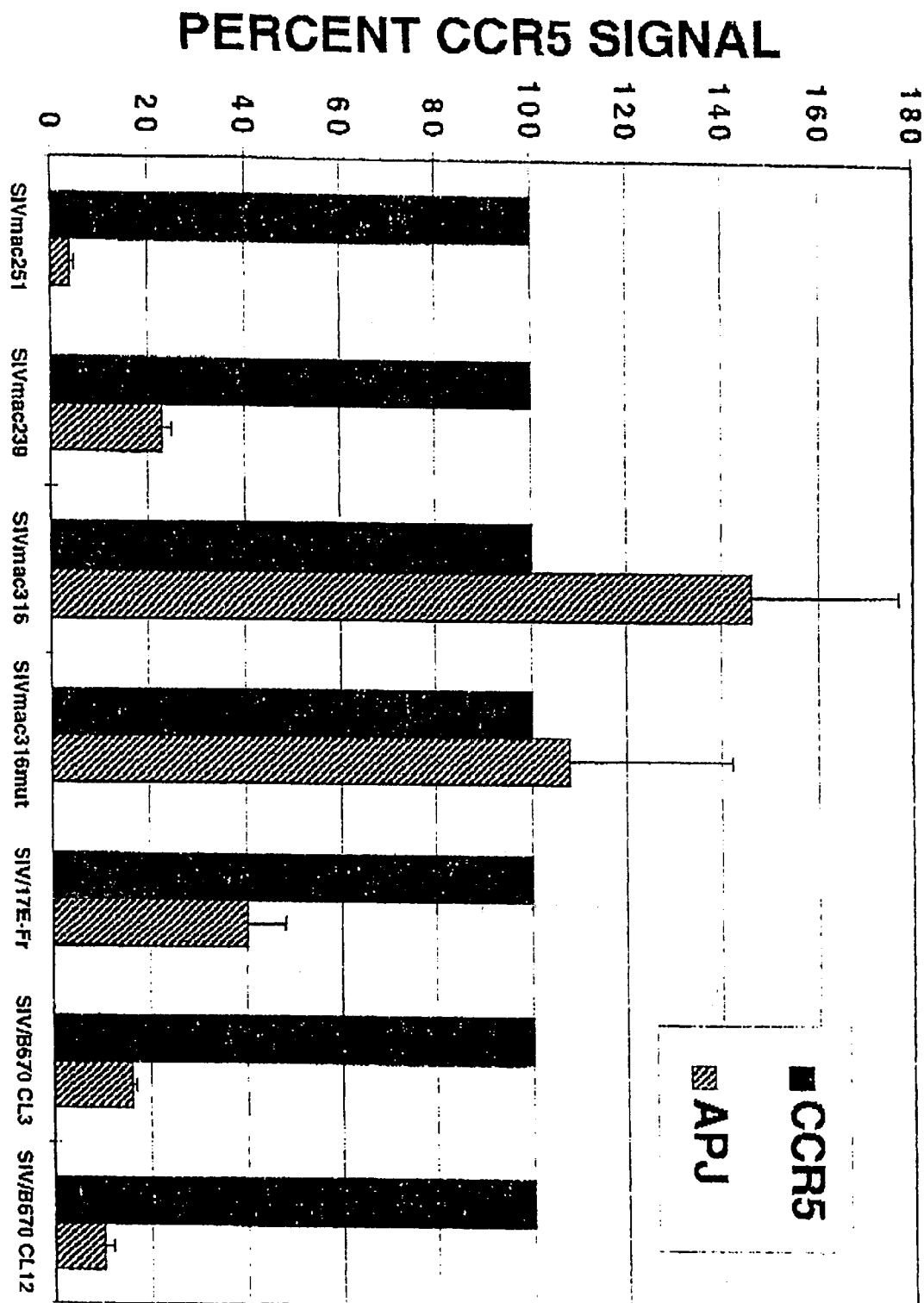
FIG. 2 is a graph showing cell-cell fusion mediated by SIV env proteins. Cell-cell fusion was determined as in FIG. 1, but using SIV rather than HIV env proteins. The results were normalized by setting the extent of fusion obtained when CD4 and CCR5 were coexpressed to 100%. The extent of fusion obtained with the different env proteins was generally 40 to 100 times above background levels (defined as CD4 alone).

The ability of APJ to support fusion by a panel of SIV envelope proteins was also examined. Unlike HIV-1, both M- and T-tropic SIV strains utilize CCR5 as a coreceptor, while CXCR4 is either not used or rarely used by SIV (Chen et al., 1997, *J. Virol.*, 71:2705–2714; Edinger et al., 1997, *Proceedings of the National Academy of Sciences, USA*, 94:4005–4010; and Marcon et al., 1997, *J. Virol.*, 71:2522–2527). In addition, the orphan receptors STRL33, GPR15, and GPR1 can be used as coreceptors by both T- and M-tropic SIV strains (Deng et al., 1997, *Nature*, 388:296–300 and Farzan et al., 1997, *J. Exp. Med.*, 186:405–411). In the instant experiments, it was determined that APJ supported fusion by several M- and T-tropic SIV env proteins at levels that were less efficient than those observed with CCR5, with the exception of the M-tropic SIVmac316 and a variant of this env protein (316mut) which efficiently used APJ as a coreceptor in cell-cell fusion assays (FIG. 2 and Table 1). Additionally, APJ typically supported fusion less efficiently than the orphan receptors GPR1, GPR15/BOB, and STRL33/Bonzo. Finally, because it was previously determined that many SIV strains can infect cells in a CD4-independent, CCR5-dependent manner (Edinger et al., 1997, *Proc. Natl. Acad. Sci., USA*, 94:14742–14747), the ability of HIV-1, HIV-2, and SIV env proteins to mediate fusion with cells expressing APJ alone was tested. The results showed that APJ coreceptor activity was strictly CD4 dependent, as cells expressing APJ alone did not support cell-cell fusion with any of the env proteins tested.

TABLE 1

| ENV | Tropism | CCR5 | CXCR4 | APJ |
|---|---|---|---|---|
| DH12 | D | +++ | +++ | + |
| RF | (D) | +++ | +++ | - |
| YU2 | M | +++ | - | + |
| JR-FL | M | +++ | - | - |
| SF162 | M | +++ | - | + |
| 91US005.11 | | +++ | - | + |
| 93BR019.10 | | +++ | - | + |
| 92UG031.7 | | +++ | - | - |
| 93BR029.2 | | +++ | - | - |
| UG37-8 | | +++ | - | + |
| TH22-4 | | +++ | - | ++ |
| RW20-5 | | +++ | - | + |
| SIVmacBK28 | | +++ | - | + |
| SIV/17E-C1 | M | +++ | - | + |
| SIVmac1A11 | M | +++ | - | + |
| SIVagmSab1.4 | | +++ | - | + |
| SIVsm62A | T | +++ | - | + |
| SIVsm62D | T | +++ | - | + |
| SIVsm543-3 | M | +++ | - | ++ |
| SIVsm543-B10 | | +++ | - | + |
| SIVsmPBj6 | | +++ | - | + |

Example 2
Determination of APJ Ability to Support Virus Infection

The ability of APJ to support virus infection was determined in order to more rigorously assess the ability of APJ to function as a coreceptor. A first assay system employed a luciferase reporter virus assay in which various env proteins were pseudotyped onto the luciferase reporter virus backbone. Luciferase reporter viruses were prepared by transfecting human HEK 293 cells with a plasmid that expresses env under the control of the CMV or SV40 promoter, and with a plasmid containing a proviral genome with an inactive env gene and the luciferase gene in place of nef (e.g. the NA4-3 luciferase virus backbone (pNL-Luc-E⁻R⁻)) (Chen et al., 1994, *J. Virol.*, 68:654–660 and Connor et al., 1995, *Virology*, 206:935–944). Target cells for infection were HEK 293 or CCCS cells with CD4 and coreceptors introduced by calcium phosphate transfection. Infections were performed in media containing 8 μg/ml DEAE dextran. Cells were lysed 3–4 days post-infection by resuspension in 0.5% NP-40 in PBS and assayed for luciferase activity.

Figure 3:
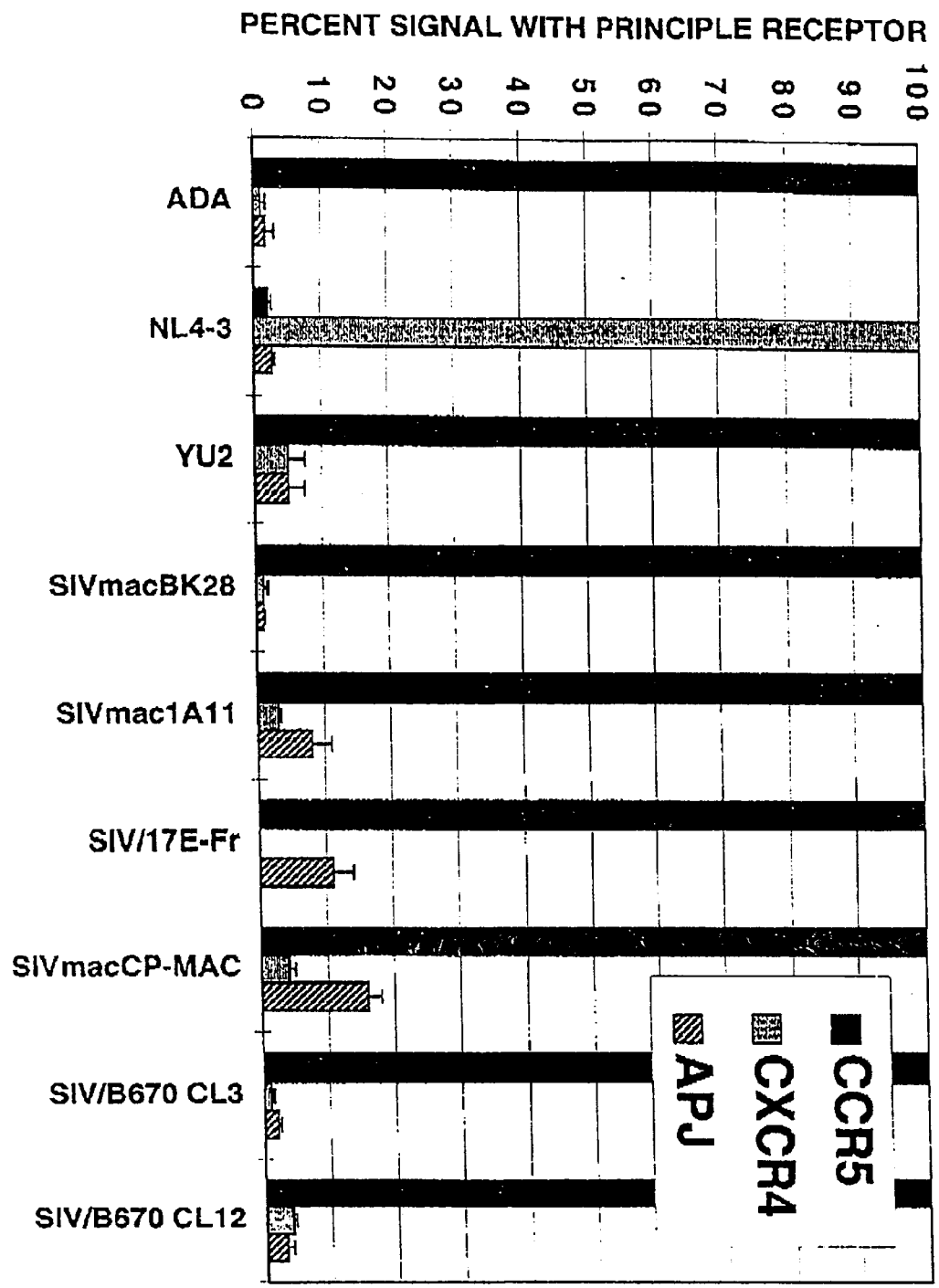
FIG. 3 is a graph showing pseudotype virus infection. HEK 293 cells expressing CD4 and the indicated coreceptor were infected with luciferase virus pseudotypes bearing the indicated HIV or SIV env protein, and luciferase activity was determined 2–3 days after infection.

Unfortunately, most env proteins which efficiently catalyzed fusion with cells expressing CD4 and APJ (such as HIV-1 89.6) could not be successfully pseudotyped. Viral env proteins that could be pseudotyped, as judged by infection of CCR5 or CXCR4 positive cells, either failed to infect cells expressing CD4 and the APJ coreceptor or did so inefficiently (FIG. 3). In some cases, env proteins that mediated fusion with APJ expressing cells at intermediate levels failed to support virus infection. For example, the virus pseudotype with the ADA env protein did not infect APJ-positive cells even though cells expressing the ADA env protein mediated fusion with APJ-positive cells half as efficiently as with CCR5-positive cells. The reasons for these assay dependent discrepancies are not clear, but may reflect the efficiencies with which various env proteins can be pseudotyped.

Figure 4:
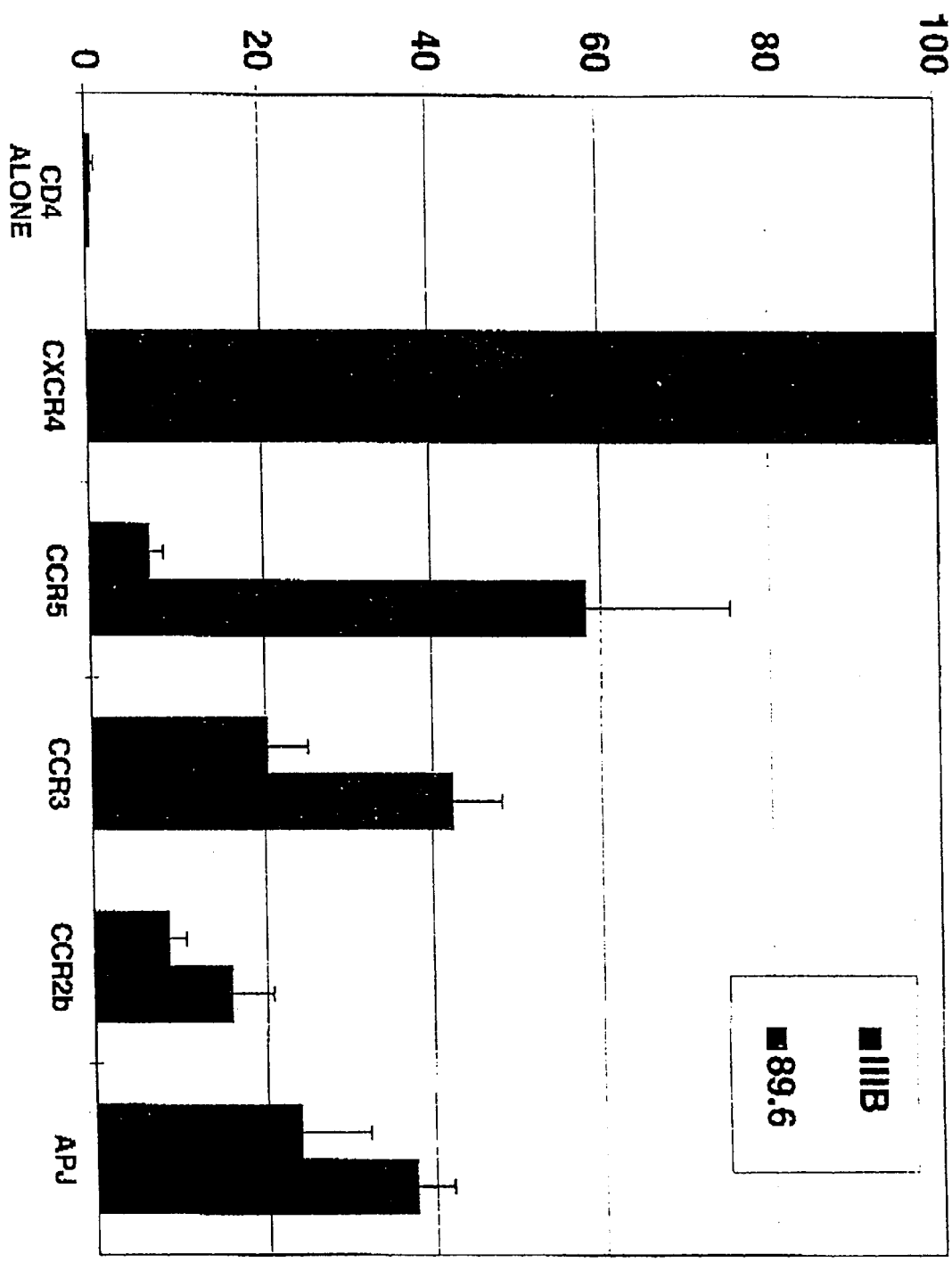
FIG. 4 is a graph showing viral infection of HEK 293 cells that express CD4 and the indicated coreceptor and that also contain a plasmid encoding luciferase under the control of the HIV-1 LTR. The cells were infected with live HIV-1 IIIB (H×B) or HIV-1 89.6. Values were normalized by setting the extent of infection obtained with either CCR5 (R5 env proteins) or CXCR4 (X4 env proteins) to 100%.

Another assay system was employed in order to test envelope proteins which could not be pseudotyped but which were able to mediate cell-cell fusion with APJ expressing cells in an efficient manner. Target HEK 293 cells that had been transfected with plasmids expressing CD4, the desired coreceptor, and luciferase under control of the viral LTR were infected with intact HIV-1 89.6 or HIV-1 IIIB (FIG. 4). Luciferase activity was measured 2 days-post infection. The results showed that HIV-1 89.6 infected APJ positive cells nearly as efficiently as cells expressing CXCR4. HIV-1 IIIB (H×B3) also infected APJ positive cells a levels well above background.

Figure 5:
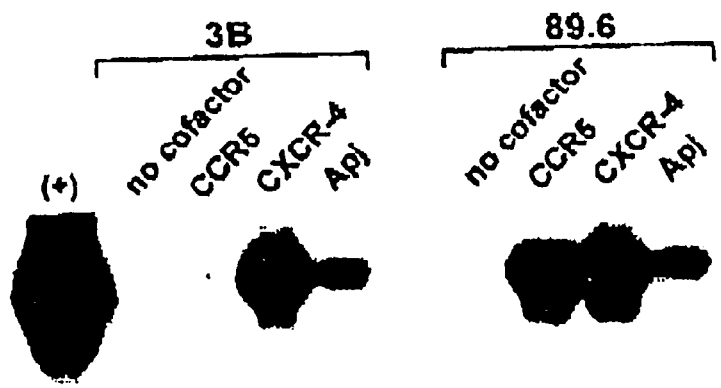
FIG. 5 is an image of a Southern blot showing the entry of virus into cells expressing CD4 and APJ. QT6 cells stably expressing CD4 and transiently expressing the desired coreceptor were infected with DNAase-treated, cell-free virus. Viral specific LTR DNA sequences were detected 2 days after infection by PCR amplification, followed by resolution of the products on a 2% agarose gel and detection of sequences using a labeled probe.

Finally, a PCR based entry assay was also employed to determine if APJ could support infection by HIV-1 89.6 and IIIB. QT6 cells stably expressing human CD4 and transiently expressing the desired coreceptor were infected with 50 ng p24 of DNAase-treated, cell-free virus. After two days, the cells were washed and lysed, and HIV-1 specific LTR DNA sequences were detected by PCR using primers LTR-plus/LTR-minus (5'-ACAAGCTAGTACCCAGTTGAGCC-3' (SEQ ID NO: 4), 5'-CACACACTACTTGAAGCACTCA-3' (SEQ ID NO: 5)). Products were resolved by electrophoresis on 2% agarose gels, transferred to Hybond N+(Amersham), and detected by using the 3'-End Labeling Biotin Kit (DuPont; probe 5'-ATCTACAAGGGACTTTCCCGC-3' (SEQ ID NO:6), followed by exposure. As shown in FIG. 5, both HIV-1 IIIB and 89.6 could enter QT6 cells expressing both CD4 and APJ, although entry was less efficient than with the major HIV-1 coreceptors.

Example 3
Examination of the of the Distribution of APJ in Human Brain by Northern Blot Analysis APJ was originally cloned from human genomic DNA, and analysis of rat tissues using a probe based on the rat homolog revealed that APJ is expressed widely in brain (O'Dowd et al., 1993, *Gene*, 136:355–360). APJ has also been shown to be expressed in some areas of the human brain (Matsumoto et al., 1996, *Neurosci. Lett.*, 219:119–122). Because of the efficient use of APJ as a coreceptor by some virus strains, APJ distribution in the human brain has been further examined by Northern blot analysis.

Membranes containing poly A⁺ RNA from various human brain regions were obtained from Clontech. The Prime-It II Random Primer Labeling Kit (Stratagene, La Jolla, Calif.) was used to label the cDNA probe with $\alpha$-$^{32}$P-dATP (3,000 Ci/mmol) using the Klenow enzyme. The $\alpha$-$^{32}$P-labeled cDNA probe was purified using Quick Spin columns (Boehringer Mannheim, Indianapolis, Ind.). The membranes were hybridized overnight with $10^7$ cpms of the labeled probe in hybridization buffer containing 25 mM Na/Na$_2$PO$_4$, 50 mM Tris pH 7.4, 6×SSPE, 0.1% SDS, 100 μg/ml single stranded DNA and 1×Denhardt's solution. The membranes were washed twice in 1×SSPE, 0.1% SDS at 42° C. for 10 minutes and changed to a high stringency wash solution of 0.2×SSPE, 0.1% SDS at 42° C. for 10 minutes. The membrane was then exposed to a Fuji Imaging plate for 4 hours. Images of the plate were captured on a BAS1000Mac Bio-Imaging Analyzer (Fuji) and processed with Mac BAS software. Images were printed on a Pictography 3000 (Fuji) digital printer.

Figure 6:
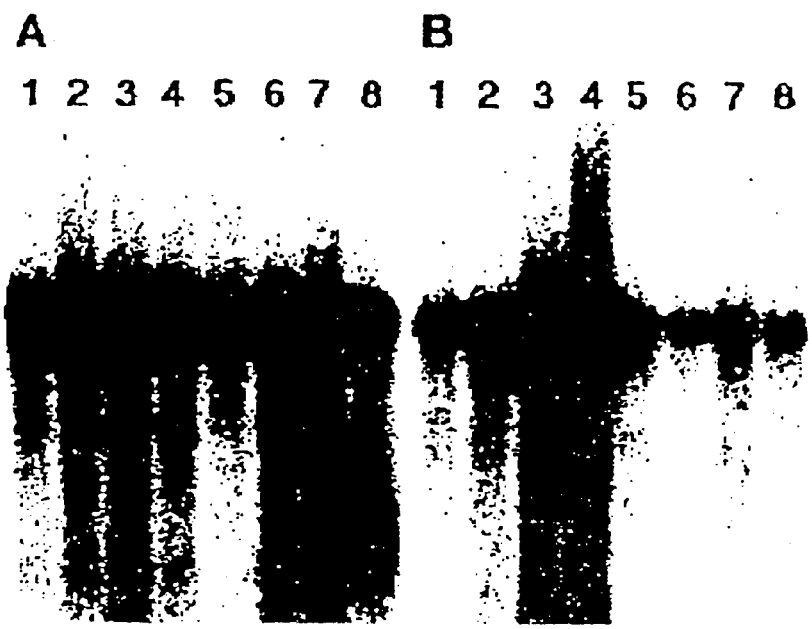
FIG. 6 is an image of a Northern blot showing the expression of APJ in human brain tissue. Membranes containing poly $A^+$ RNA from various human brain regions were obtained from Clontech and were incubated with a labeled cDNA probe specific for APJ overnight. The membranes were then exposed to a Fuji Imaging plate for 4 hours. The following tissues were examined: Panel (A): (1) Amygdala; (2) Caudate nucleus; (3) Corpus callosum; (4) Hippocampus; (5) Whole brain; (6) Substantia nigra; (7) Subthalamic nucleus; (8) Thalamus; Panel (B): (1) Cerebellum; (2) Cerebral cortex; (3) Medulla; (4) Spinal cord; (5) Occipital lobe; (6) Frontal lobe; (7) Temporal lobe; (8) Putamen.
Figure 7:
FIG. 7 is an image of a Northern blot showing the expression of APJ in human peripheral tissue. Membranes containing poly $A^+$ RNA from various human tissues were obtained from Clontech and were incubated with a labeled cDNA probe specific for APJ overnight. The membranes were then exposed to a Fuji Imaging plate for 4 hours. The following tissues were examined: (1) Spleen; (2) Thymus; (3) Prostate; (4) Testis; (5) Ovary; (6) Small intestine; (7) Colonic mucosa; (8) Total peripheral blood lymphocytes.

The results showed that high levels of APJ transcripts were present in the corpus callosum, spinal cord, and medulla. Lower levels of APJ transcripts were detected in other regions of the human brain (FIG. 6). In peripheral tissues, the APJ transcript was readily detected in spleen but absent in PBLs (FIG. 7). Lower levels of transcript were detected in other peripheral tissues.

To investigate the distribution of APJ in cells commonly used to propagate HIV-1, RT-PCR analysis was performed on a large number of cell lines and some primary cell types. A U87 cell line that stably expressed APJ was generated and used as a positive control.

Primary cells were isolated as follows. Human blood mononuclear cells (PBMC) were isolated from blood of normal volunteers using Ficoll-Hypaque, depleted of monocytes by serial adherence to plastic, stimulated with phytohemagglutinin (PHA-L, 5 µg/ml; Sigma) for 3 days and then resuspended with interleukin 2 (20 U/ml, Boehringer Mannheim Biochemicals). RNA was extracted after 3 days of PHA stimulation and also following 1 week in IL-2. Monocytes were purified from PBMC by selective adherence to gelatin followed by plastic, and then maintained in culture to allow differentiation into monocyte-derived macrophages (MDM) as previously described (Collman et al., 1989, *J. Exp. Med.*, 170:1149–1163). RNA was extracted from undifferentiated monocytes immediately after purification and from MDM after 1 week in culture.

For the isolation of total cellular RNA for RT-PCR, $5-10\times10^6$ cells were resuspended in 1 ml Trizol (GIBCO-BRL) and processed as recommended by the manufacturer. Total RNA was then treated with 1 µg (10–50 units) DNAse (RNAse-free) (Boehringer Mannheim) per 10 µg RNA for 30 min at 37° C. in the presence of 5 mM $MgCl_2$ with subsequent inactivation at 65° C. for 10 minutes in the presence of 5 mM EDTA; RNA concentration was calculated based on the $OD_{260}$. The Titan RT-PCR system (Boehringer Mannheim) was used to evaluate RNA expression patterns. Specific, internal upstream and downstream primers were used which resulted in an amplified product of 481 base pairs. The primers used were the following: forward 5'-TACACAGACTGGAAATCCTCG-3' (SEQ ID NO: 7) and reverse 5'-TGCACCTTAGTGGTGTTCTCC-3' (SEQ ID NO: 8). In order to control for contamination of the RNA sample with genomic DNA despite treatment with DNAse, all RNA samples were also amplified with Titan enzyme mix in which the RT but not PCR activity had been destroyed by treatment at 95° C. for 10 minutes (this inactivation protocol was found to eliminate the ability to amplify a RNA but not a DNA template). In each RT-PCR reaction, RNA isolated from U87-APJ stably transfected cells were included as a positive RNA control and plasmid DNA was included as a second positive control.

Figure 8:
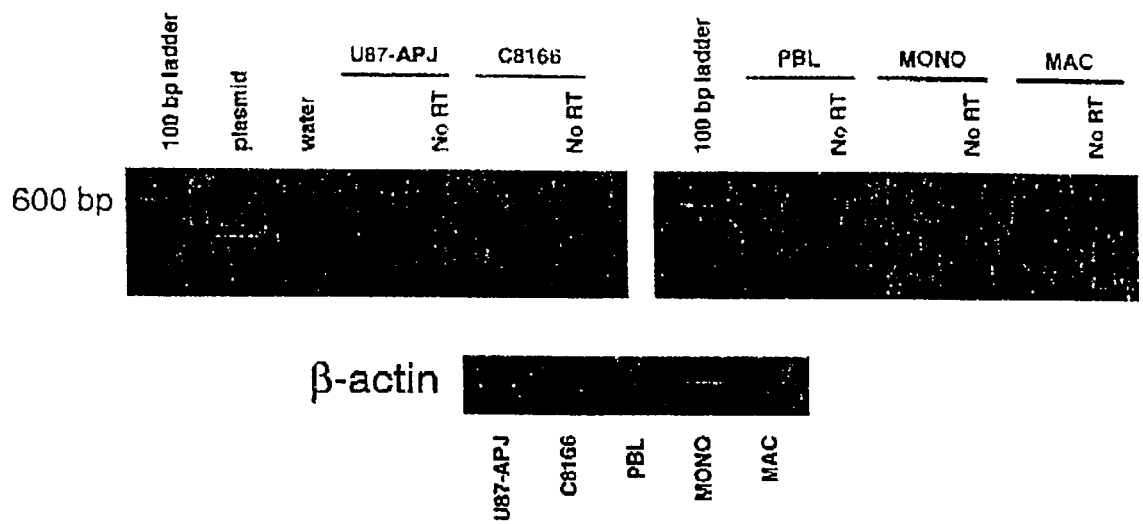
FIG. 8 is an image of a stained agarose gel showing the expression of APJ in primary cells and in T-cell lines. RNA from the indicated cells was used in one-tube RT-PCR reactions and 10 $\mu$l of each 25 $\mu$l reaction was run out on a 2% agarose gel. The size of the predicted APJ band is 481 base pairs. Both plasmid DNA and RNA isolated from U87-APJ stably transfected cells are included as positive controls and water was used as template for a negative control.

The results of the investigation of the distribution of APJ in cell lines and cell types showed that APJ was expressed in C8166 cells, but APJ-specific reaction products could not be detected in the other cell lines examined, including Jurkat, Hut78, CEMx174, and PM1 cells. Additionally, expression of APJ was not detected in PHA, PHA with IL-2, or anti-CD3 and IL-2 stimulated PBMC or in monocytes or monocyte derived macrophages (FIG. 8).

For other aspects of the nucleic acids, polypeptides, antibodies, etc., reference is made to standard textbooks of molecular biology, protein science, and immunology. See, e.g., Davis et al. (1986), *Basic Methods in Molecular Biology*, Elsevier Sciences Publishing, Inc., New York; Hames et al. (1985), *Nucleic Acid Hybridization*, IL Press, *Molecular Cloning*, Sambrook et al.; *Current Protocols in Molecular Biology*, Edited by F. M. Ausubel et al., John Wiley & Sons, Inc; *Current Protocols in Human Genetics*, Edited by Nicholas C. Dracopoli et al., John Wiley & Sons, Inc.; *Current Protocols in Protein Science;* Edited by John E. Coligan et al., John Wiley & Sons, Inc.; *Current Protocols in Immunology;* Edited by John E. Coligan et al., John Wiley & Sons, Inc.

The entire disclosure of all patent applications, patents, and publications cited herein are hereby incorporated by reference.

From the foregoing description, on skilled in the art can easily ascertain the essential characteristics of this invention, and without departing from the spirit and scope thereof, can make various changes and modifications of the invention to adapt it to various usages and conditions.

What is claimed is:

1. A recombinant eukaryotic cell transformed with an exogenous polynucleotide encoding an exogenous APJ polypeptide or an exogenous polynucleotide encoding an exogenous CD4 polypeptide, wherein the cell coexpresses APJ and CD4 polypeptides, and wherein the CD4 polypeptide and the APJ polypeptide are expressed on the surface of the cell.

2. A recombinant eukaryotic cell transformed with an exogenous polynucleotide encoding an exogenous APJ polypeptide and an exogenous polynucleotide encoding an exogenous CD4 polypeptide, wherein the cell coexpresses the exogenous APJ polypeptide and the exogenous CD4 polypeptide on the surface of the cell.

3. A recombinant eukaryotic cell according to claim 1, wherein the cell is stably transformed.

4. A recombinant eukaryotic cell according to claim 2, wherein the cell is stably transformed with an exogenous polynucleotide encoding an exogenous APJ polypeptide and an exogenous polynucleotide encoding an exogenous CD4 polypeptide.

5. The cell of claim 2, wherein the cell is a human cell.

6. The cell of claim 2, wherein the cell is a non-human cell.

7. A method for identifying a compound that inhibits interaction between an HIV virus and an APJ receptor comprising incubating
   a) a first cell line of a recombinant eukaryotic cell transformed with an exogenous polynucleotide encoding an exogenous APJ polypeptide or an exogenous polynucleotide encoding an exogenous CD4 polypeptide, wherein the cell coexpresses APJ and CD4 polypeptides and wherein the CD4 polypeptide and the APJ polypeptide are expressed on the surface of the cell with
   b) a second cell line which expresses an HIV-1, HIV-2 or SIV env protein on its surface, under conditions which promote cell fusion, in the presence and absence of a test compound, and determining whether the presence of the test compound inhibits cell fusion between the first cell line and the second cell line.

8. A method according to claim 7, wherein cell fusion is determined by detection of a reporter molecule.

9. A method according to claim 8, wherein the reporter molecule is selected from the group consisting of a radioisotope, a fluorescent compound, a bioluminescent compound, a chemiluminescent compound, a metal chelator, or an enzyme.

10. A method according to claim 8 wherein the reporter molecule is B-galactosidase or luciferase.

11. A method for identifying a compound that inhibits interaction between an HIV virus and an APJ receptor comprising incubating
   a cell line of a recombinant eukaryotic cell transformed with an exogenous polynucleotide encoding an exogenous APJ polypeptide or an exogenous polynucleotide encoding an exogenous CD4 polypeptide, wherein the cell coexpresses APJ and CD4 polypeptides and wherein the CD4 polypeptide and the APJ polypeptide are expressed on the surface of the cell with
   a test virus carrying an HIV-1, HIV-2 or SIV env protein,
   in the presence and absence of a test compound, and determining whether the presence of the test compound inhibits infection of the cell line by the test virus.

12. A method according to claim 11, wherein infection is determined by detection of a reporter molecule.

13. A method according to claim 12, wherein the reporter molecule is selected from the group consisting of a radioisotope, a fluorescent compound, a bioluminescent compound, a chemiluminescent compound, a metal chelator, or an enzyme.

14. A method according to claim 12, wherein the reporter molecule is B-galactosidase or luciferase.

15. A method for identifying a compound that inhibits interaction between an HIV virus and an APJ receptor comprising incubating
   a) a first cell line of a recombinant eukaryotic cell transformed with an exogenous polynucleotide encoding an exogenous APJ polypeptide and an exogenous polynucleotide encoding an exogenous CD4 polypeptide, wherein the cell coexpresses the exogenous APJ polypeptide and the exogenous CD4 polypeptide on the surface of the cell with
   b) a second cell line which expresses an HIV-1, HIV-2 or SIV env protein under conditions which promote cell fusion,
   in the presence and absence of a test compound, and determining whether the presence of the test compound inhibits cell fusion between the first cell line and the second cell line.

16. A method according to claim 15, wherein cell fusion is determined by detection of a reporter molecule.

17. A method according to claim 16, wherein the reporter molecule is selected from the group consisting of a radioisotope, a fluorescent compound, a bioluminescent compound, a chemiluminescent compound, a metal chelator, or an enzyme.

18. A method according to claim 16 wherein the reporter molecule is B-galactosidase or luciferase.

19. A method for identifying a compound that inhibits interaction between an HIV virus and an APJ receptor comprising incubating
   a cell line of a recombinant eukaryotic cell transformed with an exogenous polynucleotide encoding an exogenous APJ polypeptide and an exogenous polynucleotide encoding an exogenous CD4 polypeptide, wherein the cell coexpresses the exogenous APJ polypeptide and the exogenous CD4 polypeptide on the surface of the cell
   with a test virus carrying an HIV-1, HIV-2 or SIV env protein,
   in the presence and absence of a test compound, and determining whether the presence of the test compound inhibits infection of the cell line by the test virus.

20. A method according to claim 19, wherein infection is determined by detection of a reporter molecule.

21. A method according to claim 20, wherein the reporter molecule is selected from the group consisting of a radioisotope, a fluorescent compound, a bioluminescent compound, a chemiluminescent compound, a metal chelator, or an enzyme.

22. A method according to claim 20, wherein the reporter molecule is B-galactosidase or luciferase.

23. A method for identifying a compound that inhibits interaction between an HIV virus and an APJ receptor comprising incubating a first cell line which coexpresses CD4 and APJ polypeptides on the surface of the cell with a second cell line which expresses an HIV-1, HIV-2 or SIV env protein on its surface under conditions which promote cell fusion, in the presence and absence of a test compound, and determining whether the presence of the test compound inhibits cell fusion between the first cell line and the second cell line.

24. A method according to claim 23, wherein cell fusion is determined by detection of a reporter molecule.

25. A method according to claim 24, wherein the reporter molecule is selected from the group consisting of a radioisotope, a fluorescent compound, a bioluminescent compound, a chemiluminescent compound, a metal chelator, or an enzyme.

26. A method according to claim 24 wherein the reporter molecule is B-galactosidase or luciferase.

27. A method for identifying a compound that inhibits interaction between an HIV virus and an APJ receptor comprising incubating a cell line which expresses CD4 and APJ polypeptide on the surface of the cell with a test virus carrying an HIV-1, HIV-2 or SIV env protein, in the presence and absence of a test compound, and determining whether the presence of the test compound inhibits infection of the cell line by the test virus.

28. A method according to claim 27, wherein infection is determined by detection of a reporter molecule.

29. A method according to claim 28, wherein the reporter molecule is selected from the group consisting of a radioisotope, a fluorescent compound, a bioluminescent compound, a chemiluminescent compound, a metal chelator, or an enzyme.

30. A method according to claim 28, wherein the reporter molecule is B-galactosidase or luciferase.

* * * * *